US010085640B2

(12) United States Patent
Mensinger et al.

(10) Patent No.: US 10,085,640 B2
(45) Date of Patent: Oct. 2, 2018

(54) DISTRIBUTED SYSTEM ARCHITECTURE FOR CONTINUOUS GLUCOSE MONITORING

(71) Applicant: DexCom, Inc., San Diego, CA (US)

(72) Inventors: Michael Robert Mensinger, San Diego, CA (US); Eric Cohen, San Diego, CA (US); Basab Dattaray, San Diego, CA (US); Hari Hampapuram, Carlsbad, CA (US); Apurv Ullas Kamath, San Diego, CA (US); Stephen Madigan, San Diego, CA (US); Phil Mayou, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 309 days.

(21) Appl. No.: 15/152,363

(22) Filed: May 11, 2016

(65) Prior Publication Data

US 2016/0331233 A1 Nov. 17, 2016

Related U.S. Application Data

(60) Provisional application No. 62/160,475, filed on May 12, 2015, provisional application No. 62/249,043, filed on Oct. 30, 2015.

(51) Int. Cl.
*G06F 15/173* (2006.01)
*A61B 5/00* (2006.01)
(Continued)

(52) U.S. Cl.
CPC .......... *A61B 5/0004* (2013.01); *A61B 5/1495* (2013.01); *A61B 5/14503* (2013.01);
(Continued)

(58) Field of Classification Search
CPC .. A64B 5/0004; G16H 10/60; A61B 5/14503; A61B 5/14507; A61B 5/14532;
(Continued)

(56) References Cited

U.S. PATENT DOCUMENTS 5,832,448 A  11/1998 Brown
5,897,493 A  4/1999 Brown
(Continued)

FOREIGN PATENT DOCUMENTS

WO  WO 2014-040175  3/2014

*Primary Examiner* — Hamza N Algibhah
*Assistant Examiner* — Hannah S Wang
(74) *Attorney, Agent, or Firm* — Knobbe Martens Olson & Bear, LLP

(57) ABSTRACT

The present disclosure relates to techniques for receiving glucose data from a continuous glucose sensor and controlling the use and redistribution of that data so it is used in an intended manner. In one aspect, a method includes preparing data including glucose levels using a continuous glucose sensor unit; wirelessly transmitting the data relating to the glucose levels to a display device from the continuous glucose sensor unit; automatically forwarding the data relating to the glucose levels from the display device to a cloud computing architecture; and storing the data relating to the glucose levels in separate groups at the cloud computing architecture.

18 Claims, 16 Drawing Sheets

(51) Int. Cl.
*G06F 19/00* (2018.01)
*G06F 21/62* (2013.01)
*A61B 5/145* (2006.01)
*A61B 5/1495* (2006.01)
*H04L 12/26* (2006.01)
*H04L 29/08* (2006.01)
*G08B 21/02* (2006.01)
*H04M 1/725* (2006.01)
*G16H 10/60* (2018.01)
*H04W 88/02* (2009.01)

(52) U.S. Cl.
CPC ...... *A61B 5/14507* (2013.01); *A61B 5/14532* (2013.01); *A61B 5/742* (2013.01); *A61B 5/7445* (2013.01); *G06F 19/3418* (2013.01); *G06F 21/6245* (2013.01); *G08B 21/0211* (2013.01); *G16H 10/60* (2018.01); *H04L 43/04* (2013.01); *H04L 43/065* (2013.01); *H04L 67/10* (2013.01); *H04L 67/12* (2013.01); *H04M 1/7253* (2013.01); *H04W 88/02* (2013.01)

(58) Field of Classification Search
CPC ..... A61B 5/1495; A61B 5/742; A61B 5/7445; G06F 19/3418; G06F 21/6245; G08B 21/0211; H04L 43/04; H04L 43/065; H04L 67/12; H04M 1/7253
USPC .......................................................... 709/224
See application file for complete search history.

(56) References Cited

U.S. PATENT DOCUMENTS

| | | |
|---|---|---|
| 6,032,119 A | 2/2000 | Brown et al. |
| 6,101,478 A | 8/2000 | Brown |
| 6,144,922 A | 11/2000 | Douglas et al. |
| 6,168,563 B1 | 1/2001 | Brown |
| 6,368,273 B1 | 4/2002 | Brown |
| 6,442,432 B2 | 8/2002 | Lee |
| 6,477,424 B1 | 11/2002 | Thompson et al. |
| 6,480,745 B2 | 11/2002 | Nelson et al. |
| 6,669,631 B2 | 12/2003 | Norris et al. |
| 6,675,044 B2 | 1/2004 | Chen |
| 6,735,479 B2 | 5/2004 | Fabian et al. |
| 6,943,787 B2 | 9/2005 | Webb |
| 6,957,102 B2 | 10/2005 | Silver et al. |
| 7,082,334 B2 | 7/2006 | Boute |
| 7,103,578 B2 | 9/2006 | Beck et al. |
| 7,618,368 B2 | 11/2009 | Brown |
| 7,647,237 B2 | 1/2010 | Malave et al. |
| 7,689,440 B2 | 3/2010 | Brown |
| 7,814,143 B2 | 10/2010 | Brown et al. |
| 7,941,327 B2 | 5/2011 | Brown |
| 7,979,136 B2 | 7/2011 | Young et al. |
| 8,073,652 B2 | 12/2011 | Grichnik et al. |
| 8,483,967 B2 | 7/2013 | Harper |
| 8,844,057 B2 | 9/2014 | Root et al. |
| 9,141,504 B2 | 9/2015 | Greenzeiger et al. |
| 9,526,420 B2 | 12/2016 | Fish et al. |
| 2001/0031997 A1 | 10/2001 | Lee |
| 2001/0031998 A1 | 10/2001 | Nelson et al. |
| 2002/0026103 A1 | 2/2002 | Norris et al. |
| 2002/0049482 A1 | 4/2002 | Fabian et al. |
| 2002/0154111 A1 | 10/2002 | Webb |
| 2002/0178126 A1 | 11/2002 | Beck et al. |
| 2002/0193679 A1 | 12/2002 | Malave et al. |
| 2003/0109904 A1 | 6/2003 | Silver et al. |
| 2007/0287895 A1 | 12/2007 | Brown |
| 2009/0150175 A1 | 6/2009 | Young et al. |
| 2010/0031324 A1* | 2/2010 | Strich ............... G06F 21/10 726/4 |
| 2012/0197090 A1* | 8/2012 | Chen ................. A61B 5/0015 600/301 |
| 2013/0078912 A1 | 3/2013 | San Vicente et al. |
| 2013/0325352 A1 | 12/2013 | Greene et al. |
| 2013/0325504 A1* | 12/2013 | Greene ............... G01N 33/48 705/3 |
| 2014/0095577 A1 | 4/2014 | Root et al. |
| 2014/0142963 A1 | 5/2014 | Hill et al. |
| 2014/0184422 A1 | 7/2014 | Mensinger et al. |
| 2014/0187880 A1 | 7/2014 | Cohen et al. |
| 2014/0275835 A1 | 9/2014 | Lamego et al. |
| 2014/0322815 A1 | 10/2014 | Carlsgaard |
| 2015/0161344 A1* | 6/2015 | Chung .............. G06F 19/3418 705/2 |
| 2015/0170446 A1* | 6/2015 | Burba ................ G16H 10/60 340/5.52 |
| 2015/0334554 A1* | 11/2015 | Song ................. H04W 4/70 455/558 |
| 2016/0015325 A1 | 1/2016 | Lin |
| 2016/0070920 A1* | 3/2016 | Joshi ............... G06Q 30/0269 726/28 |
| 2016/0140140 A1 | 5/2016 | Darcy |

* cited by examiner

DISTRIBUTED SYSTEM ARCHITECTURE FOR CONTINUOUS GLUCOSE MONITORING

INCORPORATION BY REFERENCE TO RELATED APPLICATIONS

Any and all priority claims identified in the Application Data Sheet, or any correction thereto, are hereby incorporated by reference under 37 CFR 1.57. This application claims the benefit of U.S. Provisional Application No. 62/160,475, filed on May 12, 2015, and U.S. Provisional Application No. 62/249,043, filed on Oct. 30, 2015. Each of the aforementioned applications is incorporated by reference herein in its entirety, and each is hereby expressly made a part of this specification.

TECHNICAL FIELD

The present disclosure relates to a continuous glucose monitor for wirelessly transmitting data relating to glucose values, and controlling the display and distribution of that data.

BACKGROUND

Continuous glucose monitors have been increasing in popularity as an easy way to monitor glucose levels. Prior to the use of continuous glucose monitors, users may have found it necessary to sample their blood glucose levels several times throughout a day, such as in the morning, around lunch, and in the evening using, for example, a test strip that determines glucose levels from a small blood sample. Continuous glucose monitors replace these test strips and provide electronic monitoring and display of glucose levels.

In addition to monitoring glucose levels, continuous glucose monitors can generate and track a variety of other data relating to glucose levels. For example, a continuous glucose monitoring system can track numerous data points including patient-identifying information, timestamps, alerts established by a user, diagnostic information for an electronic unit associated with the continuous glucose monitor, and a variety of other information. The continuous glucose monitor can transmit this information to display devices so that a user can view glucose levels.

Initially, continuous glucose monitors wirelessly transmitted data relating to glucose levels to a dedicated display. The dedicated display is a medical device designed to display glucose levels, trending patterns, and other information for a user. However, with the increasing popularity of smartphones and software applications (apps) executing on smartphones, some users prefer to avoid having to carry a dedicated display. Instead, some users prefer to monitor their glucose levels using a dedicated software app executing on their mobile computing or smart device, such as a smartphone, tablet or wearable device like a smartwatch or smartglasses. By using software apps on such smart devices, the continuous glucose monitoring system can transmit the glucose and continuous glucose monitor information to other devices, software applications, and servers. These other devices, software applications, and servers can provide enhanced glucose monitoring, allow additional users to track glucose levels for a person (e.g., a parent monitoring a child's glucose levels), provide technical support relating to system operation, and can provide a number of other systems and applications access to the patient's medical data.

SUMMARY

Described in this disclosure are systems and methods for controlling the distribution and use of data having multiple categories of sensitivity (e.g., restricted, less-restricted, etc.) throughout a distributed architecture. Exemplary embodiments allow data to be sent from a continuous glucose monitor to one or more connected display devices and forwarded on to a cloud computing architecture. As noted herein, a number of challenges can arise with the distribution of data that has varying degrees of sensitivity such as medical data, including but not limited to limiting third-parties and certain system components from accessing restricted data such as proprietary, confidential or patient-identifying information while being selectively allowed to access other less-sensitive data, ensuring that unauthorized entities cannot access restricted data, and providing a system that can scale to receive, store, and selectively grant access to large amounts of data.

In some aspects, a method for securely transmitting data includes preparing data including glucose levels using a continuous glucose sensor unit; wirelessly transmitting the data relating to the glucose levels to at least one display device from a transmitter associated with the continuous glucose sensor unit; automatically forwarding the data relating to the glucose levels from the at least one display device to a cloud computing architecture; and storing the data relating to the glucose levels in separate groups at the cloud computing architecture.

Implementations of the method can include one or more of the following example features. In some implementations, the data relating to the glucose levels includes measured glucose values and diagnostic data. In some implementations, the method further includes providing, by the at least one display device, additional data with the data relating to the glucose levels, in which the automatically forwarding the data includes automatically forwarding the additional data and the data relating to the glucose levels. In some implementations, the data relating to the glucose levels includes a first set of data and a second set of data, and the storing the data relating to the glucose levels in separate groups includes storing the first set of data on a first server and the second set of data on a second server. In some implementations, the first set of data includes real-time data, the real-time data including one or more of glucose values, a current status of the continuous glucose sensor unit, or timestamps associated with measurements used to obtain the glucose values; and the second set of data includes at least one of information for calibrating the continuous glucose sensor unit and information used for technical support of the continuous glucose sensor unit. In some implementations, the method further includes encrypting the first set of data by the transmitter; encrypting the second set of data by the transmitter; decrypting and displaying the first set of data by the at least one display device; preventing the at least one display device from decrypting the second set of data; and decrypting the second set of data by the cloud computing architecture. In some implementations, the method further includes storing a first key to decrypt the first set of data by the at least one display device; storing a second key to decrypt the second set of data by the cloud computing architecture; and preventing access to the second key by the at least one display device. In some implementations, the method further includes forwarding a subset of the data relating to the glucose levels from the cloud computing architecture to a second display device, the subset of data including at least one of current and past glucose levels. In some implementations, the method further includes selectively determining, by the cloud computing architecture, whether to grant access to the first set of data and the second set of data by one or more requesting systems. In some implementations, the requesting systems include a technical support system, at least one third-party application, and a data warehouse, in which the cloud computing architecture grants the technical support system access to the first set of data and the second set of data; grants the at least one third-party application access to the first set of data; and grants the data warehouse access to the first set of data and the second set of data. In some implementations, the display device includes at least one of a smartphone, tablet, desktop computer, laptop computer, wearable display device.

In some aspects, a system for monitoring data relating to analyte levels includes a continuous glucose sensor unit configured to prepare data relating to glucose levels, the continuous glucose sensor unit including a wireless transmitter configured to transmit the data relating to the glucose levels; at least one display device configured to receive the transmitted data relating to the glucose levels and automatically forward the data; and a cloud computing architecture configured to receive the automatically forwarded data and store the data relating to the glucose levels in separate groups.

Implementations of the system can include one or more of the following example features. In some implementations, the data relating to the glucose levels includes measured glucose values and diagnostic data. In some implementations, the at least one display device is further configured to provide additional data with the data relating to the glucose levels; and automatically forward the additional data and the data relating to the glucose levels. In some implementations, the data relating to the glucose levels includes a first set of data and a second set of data, and in which the cloud computing architecture is configured to separately store the first set of data on a first server and storing the second set of data on a second server. In some implementations, the first set of data includes real-time data, the real-time data including one or more of glucose values, a current status of the continuous glucose sensor unit, or timestamps associated with measurements used to obtain the glucose values; and the second set of data includes at least one of information for calibrating the continuous glucose sensor unit and information used for technical support of the continuous glucose sensor unit. In some implementations, the transmitter is further configured to encrypt the first set of data and the second set of data; the at least one display device is further configured to decrypt and display the first set of data; the at least one display device cannot decrypt the second set of data; and the cloud computing architecture is further configured to decrypt the second set of data. In some implementations, the at least one display device is further configured to store a first key to decrypt the first set of data; the cloud computing architecture is further configured to store a second key to decrypt the second set of data; and the at least one display device cannot access the second key. In some implementations, the cloud computing architecture is further configured to forward a subset of the data relating to the glucose levels to a second display device, the subset of data including at least one of current and past glucose levels. In some implementations, the cloud computing architecture is further configured to selectively determine whether to grant access to the first set of data and the second set of data by one or more requesting systems. In some implementations, the requesting systems include a technical support system, at least one third-party application, and a data warehouse, in which the cloud computing architecture is further configured to grant the technical support system access to the first set of data and the second set of data; grant the at least one third-party application access to the first set of data; and grant the data warehouse access to the first set of data and the second set of data. In some implementations, the at least one display device includes at least one of a smartphone, tablet, desktop computer, laptop computer, wearable display device. In some implementations, the cloud computing architecture includes a plurality of servers configured to receive the data from the at least one display device, in which the data routed to a particular server of the plurality of servers is determined by a data type including real-time data and bulk data. In some implementations, the plurality of servers are configured to receive the data from the at least one display device on an intermittent basis that varies depending upon the data type. In some implementations, the plurality of servers of the cloud server architecture include at least a real-time server and a bulk data collector, the real-time server configured to receive the real-time data, and the bulk data collector configured to receive the bulk data. In some implementations, the system further includes a plurality of remote monitor display devices that receive data from the real-time server, in which the data sent to a respective remote monitor display device of the plurality of remote monitor display devices is associated with a corresponding continuous glucose sensor device to which the remote monitor display device is assigned to monitor.

Other systems, methods, features and/or advantages will become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The accompanying drawings, which are incorporated in and constitute a part of this specification, illustrate embodiments and together with the description, serve to explain the principles of the methods and systems.

DETAILED DESCRIPTION

Figure 1:
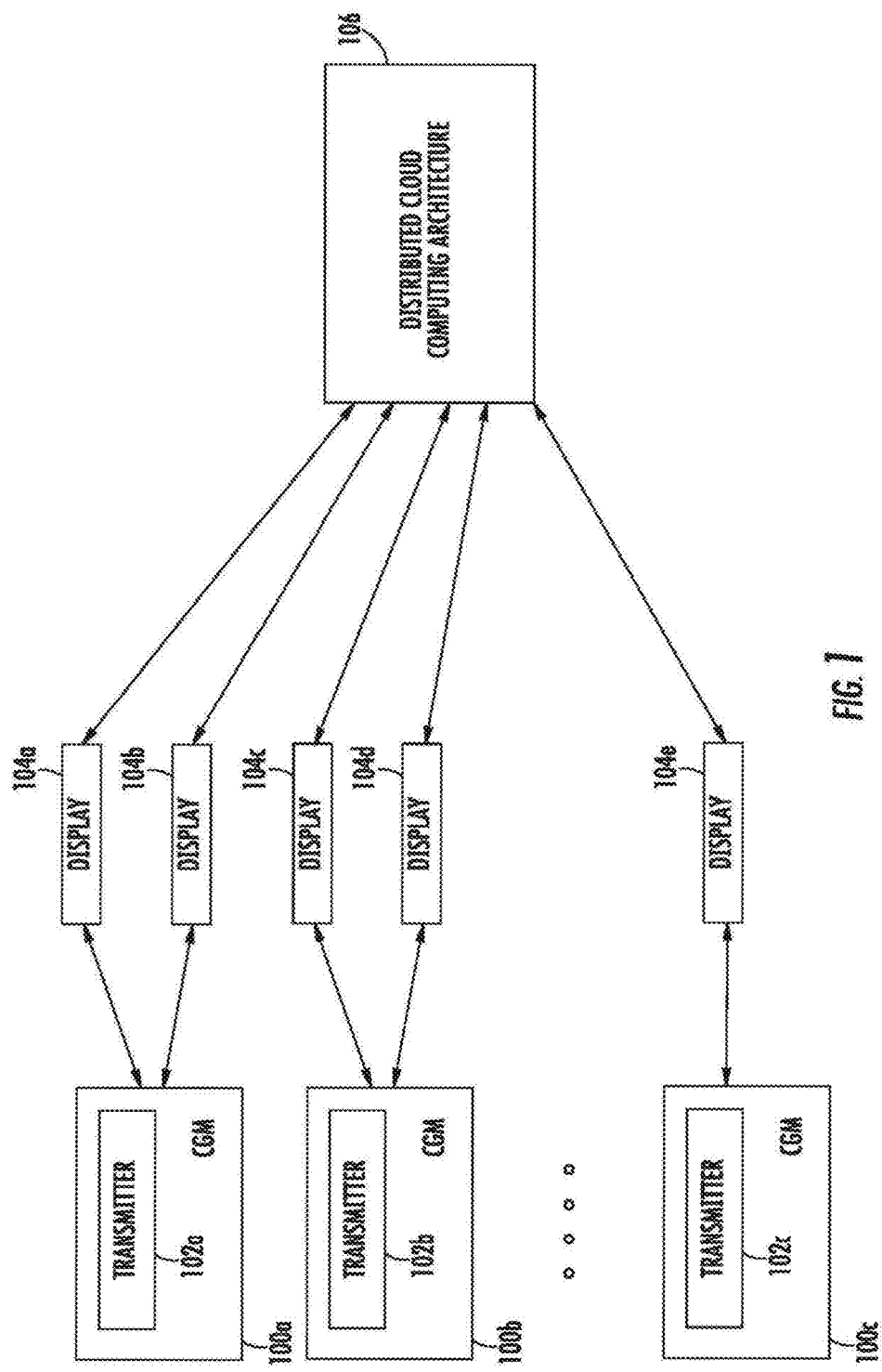
FIG. 1 illustrates an exemplary system for monitoring glucose levels and controlling access to and use of medical data.

The present disclosure relates to techniques for receiving glucose data from a continuous glucose sensor and controlling the use and redistribution of that data so it is used in an intended manner.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes¬ from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components and features that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

Distributing glucose information, related health information, and continuous glucose monitor device information throughout a system and to other systems and applications creates challenges associated with protecting patient confidentiality. The glucose information, diagnostic information, and other confidential or proprietary information are not appropriate for reproduction to all additional systems and applications. Because additional systems and applications should not have access to all of the data, it would be beneficial to separate and categorize data, and to protect the redistribution of some or all of the data in a manner that ensures patient confidentiality.

In one illustrative example, a continuous glucose monitor can transmit a glucose level, a timestamp indicating when the monitor obtained the glucose level measurement, and patient identifying information to a display. The display forwards this information to a server repository, which also stores information from a number of other patients. Some applications can request access to this information and receive the glucose level, timestamp, and patient identifying information. As an example, a patient may want their doctor's office to access this information. However, the patient identifying information is unnecessary to provide technical support for a user experiencing problems with their continuous glucose monitor. The patient identifying information, in that example, should therefore be excluded and technical support restricted from learning the identity of a patient.

Another issue that arises with regard to storing data associated with a continuous glucose monitor at a server includes how to organize and store the data. Such data can include, for example, data related to patients' glucose levels, raw or calibrated data from continuous glucose monitors, alert data including alert levels, fault detection data, and the like. Tens of thousands of patients can use continuous glucose monitors that forward large volumes of data to a server on a regular basis. The process of receiving, storing, and providing selective access to third-parties, authorized users, and additional system components creates large processing loads on the server. In one illustrative example, a continuous glucose monitor obtains a glucose level reading and an associated timestamp every five minutes. A display forwards the glucose levels and timestamps to a server for storage along with additional data that will be described below. As a result, in this example, a server receives two hundred and eighty-eight glucose levels, timestamps, and additional data from a single user per day. For twenty thousand continuous glucose monitors operating over the course of a month, the server will receive over one hundred and seventy-five million data transmissions including glucose levels, timestamps, and additional data. That same server must archive this information, control access to portions of the information, search for selected portions of information, and forward the selected portions of information to authorized entities. This creates a tremendous processing burden on the server.

Additionally challenging is that a continuous glucose monitor can wirelessly transmit data such as glucose levels, timestamps, and other associated information to multiple displays, and each display can forward the data to the server. In one illustrative example, the continuous glucose monitor transmits data to a receiver with a display as well as to a smartphone, smart watch, personal computer, tablet, or other type of display. In this example, two data streams for each user can be sent to the server, resulting in duplicative data. In addition, one display may be offline, such as when a smartphone is turned off or out of wireless range from the continuous glucose monitor, so the two data streams from two displays associated with the same continuous glucose monitor differ. The two data streams can also differ for other reasons. In one example, the two displays can use different calibration values resulting in different glucose levels based on the same data set received from a continuous glucose monitor. Therefore, it would be beneficial to organize, store, and provide accurate reproduction of data received from multiple displays.

Another challenge arises with security of transmission of the data throughout a system. While some components in a distributed architecture should be allowed to access some data, others should not. Therefore, it would be beneficial to restrict unauthorized parties from accessing data, and for limiting authorized parties to only accessing a subset of data. In addition, there can exist a great number of other devices or software applications that access data stored by the server. Considering the potential of such large numbers of other devices or software applications, it would be beneficial to provide standardized interfaces for allowing access to the data. Yet, this may be particularly difficult in the medical device field where the system may be required to obtain regulatory approval as a medical device. Once approved, changes to the system may require further regulatory approval, which can be a timely and costly process. Therefore, it would be beneficial for a modular, standardized interface that can accommodate many different third party components and adapt to differing requests from the third party components without requiring change to the system design.

The present disclosure is directed to systems and methods for controlling the distribution and use of data having multiple categories of sensitivity (e.g., restricted, less-restricted, etc.) throughout a distributed architecture. In some example embodiments, the architecture in accordance with the present technology allows data to be sent from a medical device (e.g., a continuous glucose monitor) to one or more connected display devices (e.g., a smartphone, tablet, or wearable smart device like a smartwatch or smartglasses) and provided to a cloud computing system designed to distribute the data according to varying degrees of sensitivity of the data, e.g., for medical data, proprietary, confidential or patient-identifying information, to control access to the data by third-parties and/or certain system components based on the determined degree of sensitivity. In some implementations in accordance with the present technology, such third-parties and/or certain system components would be prevented from accessing restricted data without permission while being selectively allowed to access other less-sensitive data, e.g., ensuring that unauthorized entities cannot access restricted data, and providing a system that can scale to receive, store, and selectively grant access to large amounts of data. While several examples of a distributed architecture is described for continuous glucose monitoring, other example implementations are discussed below throughout the specification, and the scope of the claims should not be limited to addressing only embodiments associated with continuous glucose monitoring.

The present methods and systems may be understood more readily by reference to the following detailed description of preferred embodiments and the Examples included therein and to the Figures and their previous and following description.

FIG. 1 illustrates an exemplary system for monitoring glucose levels and controlling access to and use of data associated with such monitoring. Such data can be defined as having multiple categories, with each category having one or more levels of sensitivity. The disclosed system of FIG. 1 can be used for storing and distributing data, wherein data in different categories or having different levels of sensitivity can be treated differently within the system. For example, data that identifies or can be used to identify a patient should not be reproduced to all third-parties. Only third-parties having proper permissions or authorizations should be able to access this data. Furthermore, other data, such as glucose levels, can be misused by third parties. As an example, third-parties receiving monitored glucose levels might make incorrect recommendations to a user on how to control their insulin pump. The system of FIG. 1 allows some data to be treated differently than others by separating categories of data, such as public data, private data, real-time data (e.g., raw or calibrated), and other bulk data, as described below. The system of FIG. 1 can allow some data to be treated differently than others by offering permission-based access to data. Furthermore, the system of FIG. 1 can store and provide access to large amounts of data. For example, the system of FIG. 1 can temporarily store some data in a cloud computing architecture, such as data within the a most recent definable time period (e.g., 15 days, 30 days, 60 days, etc.), and periodically transfer other data, such as data aged more than thirty days, to longer-term storage.

With reference to FIG. 1, continuous glucose sensor units 100*a-c* obtain a series of measurements relating to glucose levels in patients. The continuous glucose sensor units 100*a-c* can be worn, for example, in the abdomen region of patients. A small sensor can extend into the patient to obtain readings of glucose values using, for example, subcutaneous glucose or blood glucose readings. The continuous glucose sensor units 100*a-c* can also be transdermal devices, intravascular devices, or non-invasive devices.

Continuous glucose sensor units 100*a-c* include a number of components to obtain glucose measurements, store the data, calculate glucose levels, and communicate with displays 104*a-e*. The displays 104*a-e* can be dedicated receivers associated with continuous glucose sensor units 100*a-c*, e.g., including but not limited to smartphones, wearable smart devices such as smartwatches and smartglasses, personal computers, tablets, and a variety of other computing devices. Although not illustrated, continuous glucose sensor units 100*a-c* include nonvolatile memory for storing historical data regarding glucose values, a processor, a battery, and a wireless transmitter. The continuous glucose sensor units 100*a-c* include transmitters 102*a-c*, which can provide any type of wireless communications, e.g., including a Bluetooth connection, Wi-Fi connection, RF connection, and others, to communicate with displays 104*a-e* and other computing devices. The wireless communications occur, in some embodiments, between paired, authenticated devices, and use encryption and other cryptographic techniques, e.g., to ensure that communications remain confidential.

While illustrated as a single unit, portions of the continuous glucose sensor units 100*a-c* may be removable from remaining portions of the continuous glucose sensor unit. For example, reusable electronics portions of the sensor unit 100*a-c* (e.g., data transmitter and/or receiver, battery, memory, and/or processor), which may be referred to as the "transmitter", such as transmitter 102, may be removable from single use portions of the sensor unit (e.g., sensor needle) and reused with a new single use portion. Further, the continuous glucose sensor units 100*a-c* can include other components to facilitate data communications. For example, the continuous glucose sensor units 100 include wired ports, such as a USB port, Ethernet port, and others, for communicating with other devices and providing data relating to glucose levels.

The continuous glucose sensor units 100*a-c* of FIG. 1 can obtain samples at predetermined intervals, such as every few seconds, every thirty seconds, every minute, every five minutes, or on demand in response to the occurrence of an event (e.g., a command from a user, detection of a user action, such as user movement, and the like). The wireless transmitters 102a-c can be turned off or put into a low power state to conserve battery life while one or more measurements are taken over a period of time, and then wake the transmitter back up to wirelessly transmit the one or more measurements to displays 104a-e in a batch transfer. For example, the continuous glucose sensor units 100a-c wake up the wireless transmitter every five minutes, transfer data relating to glucose measurements (and any other data) generated over the last five minutes, and transfer the data to displays 104a-e. The wireless transmitters 102a-c can then be turned off again to conserve battery life. While an example of transferring data every five minutes has been provided, it will be appreciated that longer or shorter time periods can be used, and the time period can be configured by a user via displays 104a-c.

Further, to the example of FIG. 1, it will be appreciated that continuous glucose sensor unit 100a and displays 104a-104b may be used by a first patient, continuous glucose sensor unit 100b and displays 104c-d may be used by a second patient, continuous glucose sensor unit 100c and display 104 may be used by a third patient; and many other patients may use continuous glucose sensor units and associated displays. The displays 104a-e or continuous glucose sensor units 100a-c transmit data to the distributed cloud computing architecture 106, also referred to as the cloud computing infrastructure, as described in more detail below.

The data transmitted between continuous glucose sensor units 100a-c and displays 104a-e can be any type of data relating to monitoring glucose values and the operation of the continuous glucose sensor units 100a-c. For example, the continuous glucose sensor units 100a-c exchange calibration data with respective displays 104a-e on initial startup and periodically to maintain accuracy of the glucose measurements. A user may sample their glucose level using a single point glucose meter, enters the value displayed by the test kit into one of displays 104a-e, and that value is used to calibrate the associated continuous glucose sensor unit. Similarly, data can also be exchanged between other physiological monitoring devices (e.g., temperature detection device, blood pressure monitor, blood oxygen content monitor, etc.) and the displays 104a-e, or data can be exchanged between other physiological monitoring devices and the continuous glucose sensor units 100a-c.

Other examples of data exchanged include an amount of current or voltage (e.g., raw values) measured by a continuous glucose sensor unit, a converted glucose value (e.g., a calibrated value or an estimated glucose value) in, for example, mg/dL, and a timestamp associated with the time when each measurement or value was sampled, alerts related to glucose levels exceeding predetermined thresholds, detected faults in the system, firmware version, hardware version for the continuous glucose sensor and transmitter, calibration status, the time the senor was started and/or stopped, battery voltage, encryption information, a transmitter identifier number, and the like. This data can also be forwarded from a services server, e.g., such as a server associated with the manufacturer of the continuous glucose sensor unit. Although described as continuous glucose sensor units 100a-c, other medical devices may be used with the disclosed embodiments. For example, the sensor units depicted in FIG. 1 as continuous glucose sensor units 100a-c can be any analyte sensor and the transmitted data can reflect analyte values produced by the analyte sensor unit. Any data of any type transmitted between the continuous glucose sensor units 100a-c and displays 104a-e or between displays 104a-e and the distributed cloud computing architecture 106 or between any one the continuous glucose sensor units 100a-c and displays 104a-e and any other physiological monitoring device or any other system, device or person can be considered a data point.

Displays 104a-e can be a computing device comprising a display such as a visual display screen, auditory display including speakers, haptic display, and any other type of display. In some implementations, for example, displays 104a-e can be used as a dedicated display to use with the respective continuous glucose sensor units 100a-c, in which dedicated it not necessarily exclusive for displaying data from the continuous glucose sensor units. For example, the combination of a continuous glucose sensor unit 100 and a display 104 can, in one embodiment, be an approved medical device, such as a class III medical device.

Display 104 includes a processor for calculating glucose levels based on received measurements, memory for storing glucose levels, ports for wired communications, and wireless communication circuits, e.g., such as Bluetooth, Wi-Fi, or RF circuits. In implementations, for example, displays 104a-c receive data relating to glucose levels from continuous glucose sensor units 100a-c at predetermined time intervals. In addition, display 104 can determine a historical trend of whether a user's glucose levels are trending down, remaining stable, or increasing. Displays 104a-e present glucose readings over time so a user can easily monitor glucose levels, and display an actual value of the current glucose level.

Displays 104a-e can also be any type of display associated with a personal computer, tablet, or smartphone that executes applications for displaying data relating to glucose levels. As a result, displays 104a-e includes hardware components typically associated with personal computing devices, including processor(s), memory, wireless connections, a USB port, and others.

Displays 104a-e can execute a plurality of applications, e.g., software applications ("apps") comprising instructions executable by a processor, that relate to glucose monitoring, health information, exercise activity, controlling and monitoring insulin injections, eating habits, and others. In one embodiment, continuous glucose sensor unit 100a transmits multiple streams of data, and display 104a receives the same data that continuous glucose sensor units 100a transmits to display 104b. Display 104a can be a dedicated display associated with the continuous glucose sensor unit 100a, and display 104b can be a general-purpose computing device, such as, for example, a smartphone or the like. The example smartphone can execute one or more applications dedicated for use with the continuous glucose sensor unit 100a, as well as other applications. The dedicated application controls the use of the medical data received from the continuous glucose sensor unit 100a, e.g., such as the distribution of the data to other applications executing on the smartphone to preserve confidentiality and user preferences, as described in more detail below. For example, the dedicated application can also be connected to and provide information to other third-party applications.

In some embodiments, displays 104a-e receive and display the entire set of data received from respective continuous glucose sensor units 100a-c. For example, display 104 displays actual glucose levels associated with measurements taken by the sensor. The continuous glucose sensor unit 100, an operating system executing on display 104, or dedicated application executing on display 104 (as described above)

can restrict third-party applications from receiving and displaying actual glucose levels. In some implementations, for example, the third-party applications instead can receive a more generic indicator of glucose levels, such as whether glucose levels are low, normal, or high. Additional details regarding the types of data that can be sent to and displayed by display 104 will be provided below.

Figure 3:
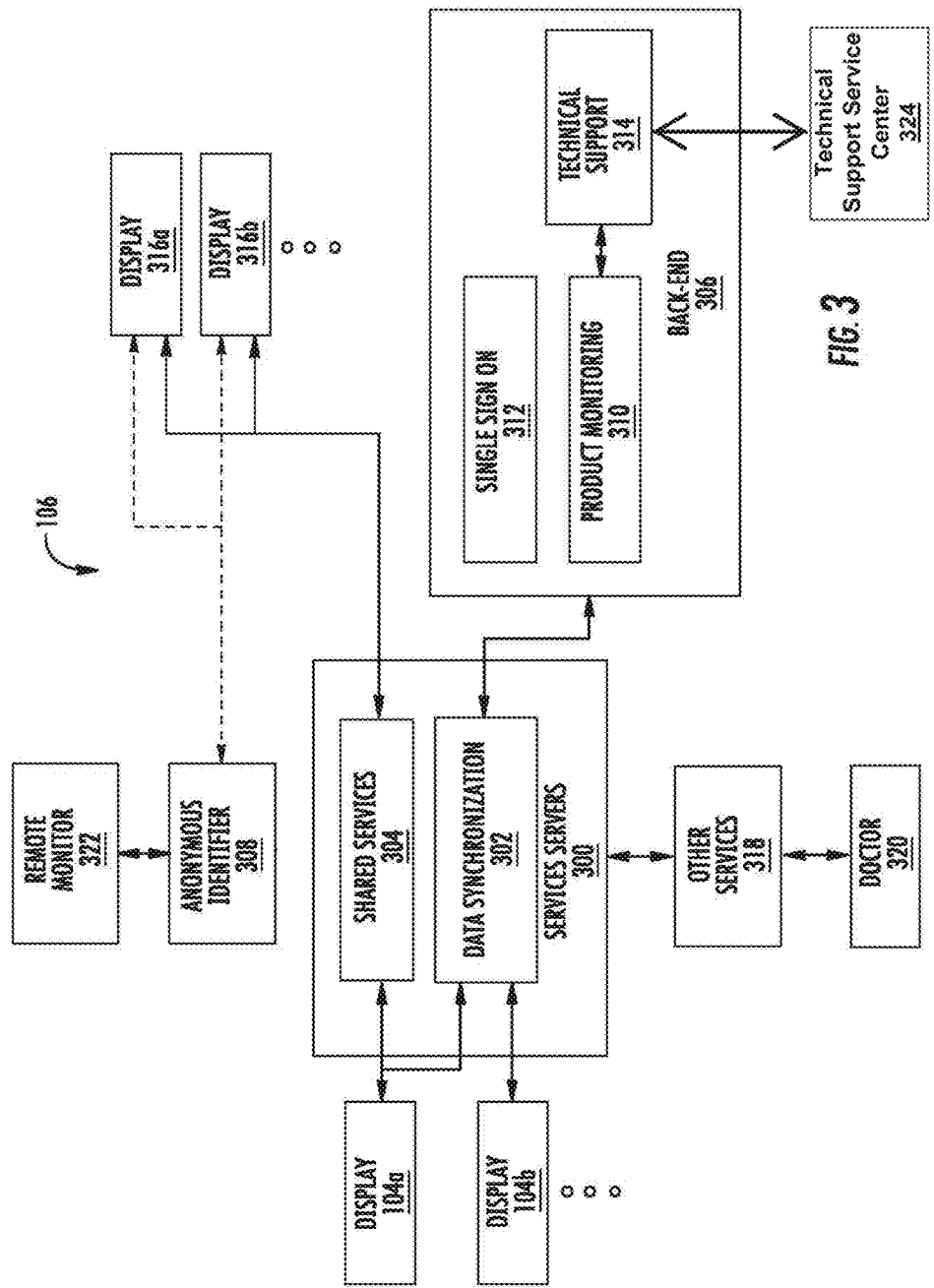
FIG. 3 illustrates an exemplary embodiment of a system in accordance with a cloud computing architecture of the present technology.

The displays 104*a-e* or continuous glucose sensor units 100*a-c* transmit data to the distributed cloud computing architecture 106. The distributed cloud computing architecture 106 organizes, stores, and provides access to the data by other computers, applications, and third-parties. The distributed cloud computing architecture 106 includes plurality of different servers, storage systems, and software applications executing both locally and across distributed networks. FIG. 3 provides a diagram of an example embodiment of the distributed cloud computing architecture 106, and is discussed later in this patent document.

Communications within the system can be subject to a number of security protocols. For example, communications can be encrypted and secured, such as HTTPS and SSL communications. The cloud computing architecture 106 can include a firewall that only allows specific and secure communication on defined ports. In addition, a system including the distributed cloud computing architecture 106 can use authenticated sessions with a login with name and password for web service methods that a user or remote monitor (described herein) would use to gain access to read or alter their information. The login names and passwords are stored in a secure fashion using hashing and encryption, and patient data including all data posts from the displays can be likewise encrypted and stored in a secure fashion by the cloud computing architecture 106.

Another security measure includes using an authenticated session that times out after a short period of inactivity and also can have a maximum length. Servers can keep an audit trail or history log of all access to the system and all changes made to the system. In addition, third parties accessing data stored by the cloud computing architecture 106 can be required to authenticate themselves and may also be further restricted to only access patients they already know. That is, in some examples, a consumer's privilege may require them to already know the patient's internal identifier with the system which would have already been provided by a patient initiated exchange of any identifying information with that consumer.

Figure 2:
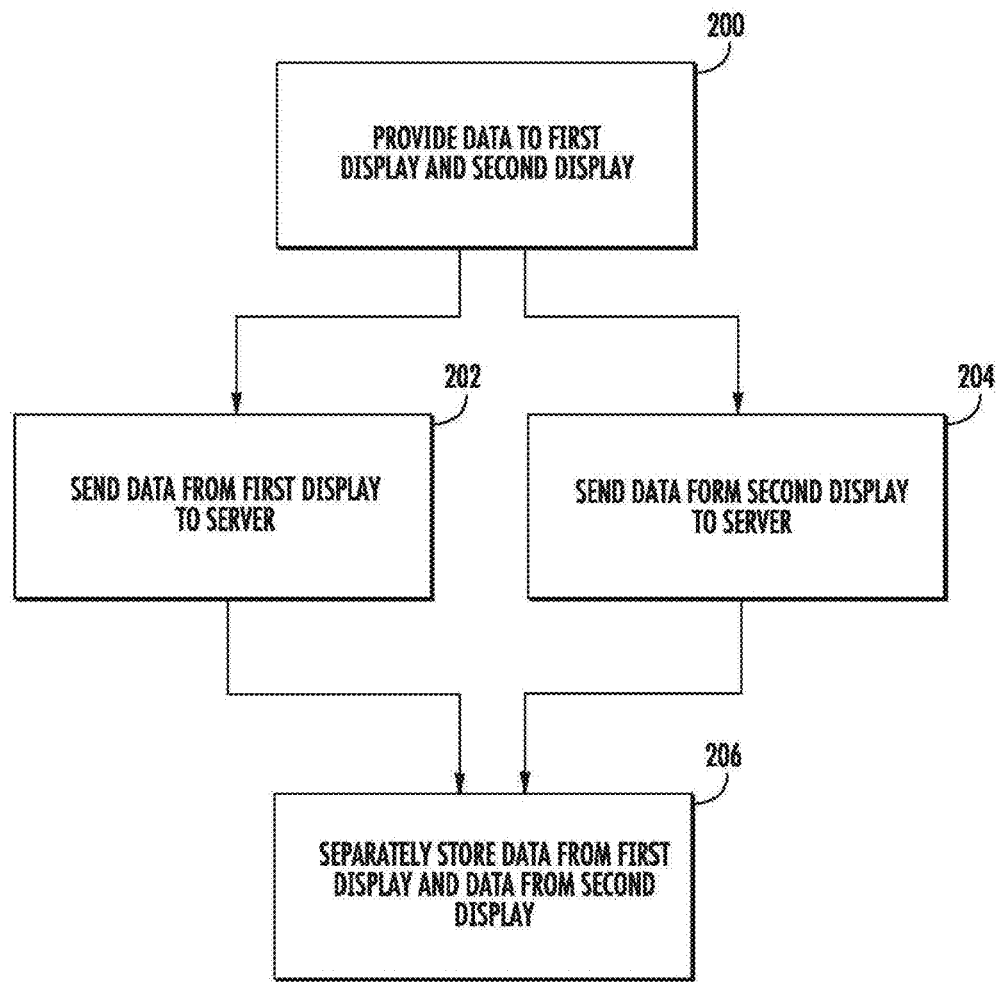
FIG. 2 illustrates an exemplary method for providing data streams to a cloud computing architecture.

FIG. 2 illustrates an exemplary method for separately transmitting and storing data streams. Given that a system in accordance with the disclosed technology may support tens of thousands of continuous glucose sensor units 100 transmitting data to the cloud computing architecture 106, where each of which can send data through multiple displays 104, the processing demands may be too great for the cloud computing architecture 106 to receive a single data stream and separate out the portions that should be assigned to different categories (e.g., public versus private). One solution is to separate the data streams out prior to transmission to the cloud computing architecture 106, allowing the cloud computing architecture 106 to separately store the data streams for quick retrieval. Although this can result in redundant data, that may be preferred because it allows the cloud computing architecture 106 to compare, for example, public streams received from both a first and second display device to determine if the two match. If any discrepancies exist, technical support can determine if there is an issue with the system operation and provide a solution. For example, calibration errors with a display 104*a-e* may be detected by comparing the data streams received from separate displays among displays 104*a-e*.

Another challenge that can arise is the server of the distributed cloud computing architecture 106 being able to quickly retrieve the data. Large numbers of data streams can feed into the cloud computing architecture 106, making fast retrieval an issue. Therefore, it would be advantageous to track the data streams and allow data to be retrieved from a given point in time.

In FIG. 2, a continuous glucose sensor unit (e.g., continuous glucose sensor unit 100*a*) provides data to a first display (e.g., display 104*a*) and a second display (e.g., display 104*b*) at process 200 automatically or in response to a request from either of the two displays. The continuous glucose sensor unit 100*a* separates the data into two streams: a public data stream and a private data stream. For example, generally, public data includes information that is presented to a patient in charts or reports such as glucose values, monitor/calibration values, time adjustments, event entries by a patient (like meals, carbs, exercise, etc.), when sensors were started/stopped, which transmitter was used and when, and the like, while private data generally comprises information about the system and devices that comprise the system such as battery levels, screen durations, error logs, raw sensor signals, proprietary algorithm input/output, stack dumps of memory, and the like.

Public data and private data can comprise one or both of real-time data and bulk data. Bulk data can include, for example, data points such as system software version information, diagnostic information, other proprietary data and stored readings such as glucose levels recorded over a time period such as one hour, two hours, etc.; while real-time data can include, for example, data points such as monitored glucose levels, timestamps associated with monitored values, glucose monitor status, and the like. Generally, real-time data is data that is transmitted by the continuous glucose sensor unit 100 or display 104 as it is created or shortly thereafter (e.g., periodically every one minute, five minutes, 10 minutes, etc.), while bulk data is data that may be stored on the continuous glucose sensor unit 100 or display 104 for a longer period of time than real-time data (e.g., one hour) and transmitted less frequently than real-time data. As described in more detail below, some data (bulk or real-time, private or public) can be encrypted while other data is not.

Furthermore, the displays 104 can transmit data at different times. For example, the displays 104*a-e* can send real-time and bulk data to the cloud computing architecture 106. In some implementations, both real-time and bulk data can be sent to the cloud computing architecture 106 on a periodic basis, with each type of data having a different, or the same, update period. For example, real-time data can be provided every five minutes to the cloud computing architecture and bulk data being provided hourly. Bulk data and real-time data transmitted from a continuous glucose sensor unit 100 to a display 104 may be the same bulk data and real-time data that is transmitted from the display 104 to the cloud computing architecture 106, or it may be different. For example, the bulk and real-time data transmitted from the display 104 to the cloud computing architecture 106 may include information about the display 104 or user interactions with the display 104. These are only exemplary update time periods and any time period is contemplated by embodiments disclosed herein.

At processes 202 and 204, the first display 104*a* and the second display 104*b* can separately send their data to a server in cloud computing architecture 106. The data can include a private header, a private data section, a public header, public content, and/or metadata describing the timing of the post and the display making the post. The first and second displays 104a-b can send the data automatically or in response to a request from the cloud computing architecture 106. The displays 104-b can also add additional data to the data received from the continuous glucose monitor 100a prior to transmission.

The displays 104a-b can send the data to the cloud computing architecture 106 upon receipt or after gathering data for a period of time. For example, the continuous glucose monitor 100a can provide bulk data to the display 104a hourly, and the display 104a can collect the bulk data for three hours before providing it to the cloud computing architecture 106.

In some implementations, because multiple displays 104a-b associated with the same continuous glucose monitor 100a provide data, the cloud computing architecture 106 may receive redundant data from multiple sources. However, the data may not actually be redundant, as it may be slightly different depending on the time at which the data was obtained by a display 104. For example, one display 104a might have been out of transmission range and therefore received backfilled data, as described below. The other display 104b might have received the data as scheduled from the continuous glucose monitor 100a. All or some of the data can be stored separately in data streams on both or either of the display 104 and the cloud computing architecture 106. This allows for an audit trail to determine what data came from which device and when.

Furthermore, different alerts can set on each display device 104a-b. For example, a user might want their phone to provide alerts during the day and their receiver display to provide alerts at night. For example, when a user misses an alert, technical support can access the data stream associated with the particular display from which the user should have received an alert, and determine whether that display received the data in real-time or as backfilled data due to missing one or more transmissions from the continuous glucose sensor unit. If the missed alarm came when the display missed transmissions, the display did not have the data upon which to issue an alarm, allowing technical support to diagnose the issue. Backfilled data can be tagged differently by the display from real-time data to distinguish it for the cloud computing architecture 106. The tag can come in metadata so the cloud computing architecture 106 does not have to separately examine the data to determine if it was obtained in real-time or as backfilled data. Additional examples and description of backfilling data are provided below.

At process 206, the cloud computing architecture 106 separately stores the data from the first display 104a and the second display 104b. The data can be stored using metadata by providing a timestamp at which time the data was received at or posted to the cloud computing architecture 106. Accordingly, the cloud computing architecture 106 tracks the time at which the last post was received from a particular display device. The post might contain new data or data that was previously sent, dropped in transmission due to an error or other system malfunction, and then retransmitting. Metadata allows the display and the cloud computing architecture 106 to track the last attempted message transmission from the display and received message transmission by the cloud computing architecture 106. The one or more servers of the cloud computing architecture 106 need not examine the actual data that was transmitted but instead rely on the metadata to efficiently store and subsequently retrieve information.

When new data records are created in the system, multiple other computers and services, having proper permissions or authorizations, can be alerted about this data by requesting notifications from the cloud computing architecture 106. For example, a remote monitor device, operable by a remote monitor user remotely monitoring the glucose state of the user of the continuous glucose sensor unit 100, can receive information about glucose levels by requesting notifications of glucose levels for the specific patient that the remote monitor device is monitoring through the cloud computing architecture 106. Third-party applications can therefore obtain public information, including the glucose levels, or other information that they have been provided authorization to receive, whereas a technical support team can also access proprietary private data.

FIG. 3 illustrates an exemplary embodiment of a system in accordance with cloud computing architecture 106. There are a number of challenges associated with receiving and storing large volumes of data. One such challenge is simply the volume of data. Receiving data from displays 104a, 104b on a periodic basis, such as every five minutes, presents a large load on servers to store the data. This may be compounded by thousands of additional displays associated with other patients all transmitting data to the same server. The cloud computing architecture 106 can both, store long-term data that can be used by third-parties, technical support, and other systems, and provide fast access for recent data from a large number of patients. In addition, security issues arise for receiving the data and storing it in a secure fashion, and ensuring that only authorized devices obtain access to the data. Further, some data will be sent through a display but it may be desired that the display not be able to access it. An example is system diagnostic information sent from a transmitter to a server via a phone that can be used by technical support but is proprietary and should not be displayed to a user. The system of the cloud computing architecture 106, e.g., depicted in FIG. 3, can allow different data to be treated differently, with varying levels of access by different system components.

In the example embodiment shown in FIG. 3, cloud computing architecture 106 includes services server 300 and/or back-end computer architecture 306. Displays 104a and 104b transmit data to services server 300. The services server 300 provides the functions for coordinating storage, retrieval, and notifications relating to glucose levels in the system. In one embodiment, the displays 104a, 104b transmit data to the services server 300 using, for example, HTTPS web services. The data includes, for example, glucose values, raw data, diagnostic data, and other types of information such as exercising information or other health-related information. The displays 104a and 104b send the data to the services server 300 automatically in some implementations. The data can include data from the continuous glucose sensor units 100 as well as additional data added by displays 104.

The displays 104a-b can send more than one category of data. For example, the displays 104a-b can send both public and private data, as real-time data (e.g., glucose values, event entry information, sensor start/stop, and associated timestamps) and bulk data (e.g., calibration, tech support-related info, alert timing related info), as described herein.

Real-time data can be provided, for example, every five minutes from continuous glucose sensor units 100 and/or displays 104. Bulk data can be provided, for example, once every hour from continuous glucose sensor units 100 and/or displays 104. In some implementations, bulk data includes internal system data, such as system operation data, that typically would not be provided to any third-parties. The real-time data and bulk data points can be different or overlapping. For example, bulk data can also include glucose values that are also real-time data values. The data can be sent directly from one display 104, such as a smartphone, to another type of the display 104, such as a personal computer or other computing device, that uploads the data to the services server 300. For example, in some embodiments, the display 104a could be a smartphone or a dedicated receiver device that receives the data from the continuous glucose sensor unit 100a, and the display 104b can be a personal computer, in which the smartphone or receiver provides the data to the personal computer, and the personal computer uploads data through a wired or wireless link. In other embodiments, the display 104a can be a dedicated display device associated with the continuous glucose sensor unit 100a that receives the data from the continuous glucose sensor unit 100a, and when it is to provide the data to the services server 300 or via the personal computer, it does so via a cradle communication device ("cradle"). For example, the dedicated display device can be placed in the cradle to connect the two devices. The cradle can include a network connection for uploading data to services server 300. In another embodiment, display 104b is a smartphone and it uploads data using an application. The real-time and bulk data can be synchronized with the services server 300 in different manners, such as at different time intervals, to facilitate separate storage and retrieval of real-time and bulk data by the cloud computing architecture 106.

In one embodiment, the transmitter 102 in a continuous glucose monitor 100 can separate bulk data and real-time data. The transmitter 102 can encrypt all or a portion of the bulk data and pass it through the associated display 104 to the services server 300 using a key stored on the transmitter 100. In some embodiments, the display 104 does not have a decryption key for the encrypted bulk data, and therefore acts simply as a pass-through for encrypted bulk data, but the shared services server 300 and back-end 306 can include the decryption key for encrypted bulk data. The transmitter 102 can also encrypt all or a portion of the real-time data using, for example, Bluetooth encryption or other techniques, and the display 104 can receive the real-time data, decrypt some or all of it for use and display, and forward the real-time data to shared services server 300 for storage.

Services server(s) 300 stores data for a predetermined amount of time, such as thirty days, and synchronize data to other devices, applications, and outside companies, along with the back-end computer(s) 306. The services server 300 and back-end computer(s) 306 can employ different levels of security for different types of data. In the example embodiment shown in FIG. 3, the services server(s) 300 includes shared services server 304 and data synchronization server 302. Shared services server(s) 304 stores the real-time data separately from the bulk data. For example, the displays can send the data separately or together, and the data can be separated into real-time and bulk data by the continuous glucose sensor unit 100, the displays 104, or the services servers 300. In one embodiment, the shared services server 304 stores data for only a predetermined amount of time. For example, this allows fast searching and access to shared data, and also limits the amount of data stored on shared services server 304. In some implementations, shared services server 304 only stores the data for past 30 days, allowing data to be stored for only as long as others devices would need to retrieve the data. In other implementations, the shared services server 300 can store data for time periods greater than or less than 30 days.

The services server 300 supports gathering the data posts on a patient-by-patient, and stream-by-stream basis. A client, such as a patient's display 104, device associated with other service 318, a remote monitor devices, or other system component can subsequently request data by asking for a specific range of data for each patient. The range of data can be based on the time the data was posted to the server. In some implementations, each transmission of data by a display can be assigned to a posting identifier. A request can be made to obtain all data posts that came after a posting identifier that can also be tracked by the client.

In some implementations, the system in accordance with embodiments of the cloud computing architecture 106 maintains separate record "streams" of posted information for each patient's source display 104, such as a smartphone and/or a receiver dedicated to use with the continuous glucose sensor unit 100. Each post can identify the source type by indicating which display posted the data. This will lead to duplicate posting of patient data, from multiple sources. The services server 300, in some implementations, separately stores these streams of data posts to reduce the complexity on the posting display devices by allowing the display devices to create incremental posts relative only to their own self-contained contiguous data. Consumers may then maintain or report on the differences between the streams or may combine the contents of the streams as desired/required.

Examples of other devices that would access recent data through shared services server 304 include remote monitors 322 that receive data in real-time. A remote monitor 322 is a person who monitors the glucose levels of another patient. The remote monitor 322 is able to monitor the glucose state of the patient using a display 316, such as a smartphone, tablet, personal computer, etc. that can be in communication with the services server(s) 300. For example, the remote monitor 322 can be a parent or guardian that accesses and monitors the glucose levels of their child using display 316a and/or 316b operable by the remote monitor 322. In some implementations, the display 104a of a patient transmits glucose data to shared services server 304, which stores the glucose data for a period of time, e.g., up to thirty days. Display 316a of remote monitor 322 requests and obtains permission to access the glucose data for a particular patient, and requests the glucose data from shared services server 304.

One challenge that may arise with remote monitors 322 is that storing any identifying information for the remote monitor could place those interactions under government privacy laws and regulation such as, for example, HIPPA regulations based on the Health Insurance Portability and Accountability Act (HIPPA) in the United States or other analogous laws or regulations in other countries. It would be preferable to avoid storing non-patient (i.e., remote monitor 322) information in the cloud computing architecture 106 to avoid implicating any privacy law or regulation. Accordingly, in some embodiments, the cloud computing architecture 106 does not receive or store any of a remote monitor's personal information. Instead, the remote monitor 322 can be assigned a digital signature or other secure anonymous identifier 308 that is associated with the remote monitor 322, but the relationship is not stored in the cloud computing architecture 106. For example, the registration process for a remote monitor 322 can result in the generation of a unique number that is an anonymous identification of the remote monitor user. Communications within the system in accordance with embodiments of the cloud computing architecture 106, such as between the shared services server 304 and a remote monitor's display device 316a use the anonymous identifier 308 instead of information that would identify the remote monitor 322.

In some embodiments, the cloud computing architecture 106 includes back-end computer architecture 306, e.g., such as one or more servers in communication with the services server(s) 300. The back-end server(s) 306 can receive real-time data from shared services server(s) 304 and bulk data from data synchronization server(s) 302. In some implementations, back-end server(s) 306 stores historical data over thirty days old and receives requests for access to data through other services devices 318 that is more than thirty days old.

The back-end server(s) 306 can function as a data warehouse that can store data either permanently or for longer periods of time for archival purposes. In some embodiments, for example, a technical support unit 314 provides automated technical support to users and patients for any issues with system operation. Technical support unit 314 receives glucose data and other real-time and bulk data and can permanently store the data to assist with future technical support issues. For example, a patient establishes alerts on displays 104a, 104b for when glucose levels cross a defined level or experience a defined rate of change. When an alert fails to deliver on the display 104 and the patient thereby misses the alert, the patient may call a technical support service center 324 to determine why the alert did not issue. Similarly, for example, the patient may have the issue addressed and/or resolved automatically by the technical support unit 314 of the back-end server(s) 306. In this regard, the technical support service center 324 may merely provide a human interaction for the patient in addressing and/or resolving the issue via the technical support unit 314. Technical support unit 314 can determine why the patient did not get an alert. In one example, the data might have been missed by display 104a because it was out of wireless range from the continuous glucose sensor unit 100, so the display 104a did not have the data that should have issued the alert. In such instances, however, the data could have been subsequently backfilled into the display 104a, as described in more detail below, so the patient looking at the display 104a believes the display 104a had the data at the correct time.

Back-end server(s) 306, e.g., including technical support unit 314, stores an indication of whether data was received by each display 104a, 104b in real-time or as part of a backfill process. By determining that the data in a display 104a was backfilled, technical support unit 314 can notify the patient that their device did not have the data at the relevant time the alarm should have issued. Similarly, for example, a technical support service in communication with the technical support unit 314 of the back-end server(s) 306 can notify the patient that their device did not have the data at the relevant time the alarm should have issued. The cloud computing architecture of FIG. 3 therefore distinguishes data based on whether it was received by a particular device, such as display 104a, display 104b, services server(s) 300, and others, in real-time or as part of a backfill process.

In the embodiment shown in FIG. 3, back-end server(s) 306 also includes a product monitoring server 310 that monitors use of products, issues updates to continuous glucose sensor units, and updates software on displays and other system devices. As an example, product monitoring server 310 can determine when a sensor associated with a patient's continuous glucose sensor unit 100 should be replaced and automatically send an e-mail to the patient as a reminder to order a new sensor.

In the embodiment shown in FIG. 3, back-end server(s) 306 also includes single sign on server 312. Single sign on server 312 provides a single sign-on for patients and users accessing a number of different applications and the system. For example, if the system were comprised of separate systems, applications, and components, the user experience may not be seamless, as the user would need to log into separate systems. In an illustrative example, a display 104 can execute an application used to monitor continuous glucose levels and an application for controlling insulin injections. The application for controlling insulin injections requests glucose information, and therefore may require two or even three separate logins: one for the application for monitoring glucose levels, one for the application for controlling insulin injections, and one to access glucose levels through the insulin injection application. This may be cumbersome for a user. One example solution to the challenge in accordance with the disclosed technology is having the application for monitoring glucose levels open other applications in a web view, allowing use of a single sign-on so that a user enters login information once and does not need to reenter information as a user is directed to other modules of the system. For example, icons can be provided within the continuous glucose monitoring application for other applications, such as an application for viewing reports with more detailed statistical information regarding glucose levels. When the user selects the icon, the application launches a web view. In this example, the web view request can bypass the shared services server 300 to provide a virtually seamless experience for a user to access other services by directly accessing a server that hosts the second application.

Accordingly, the smartphones and other displays can log into the system through the cloud infrastructure using single sign on server 312. For example, a transmitter identifier can be printed on a continuous glucose sensor unit 100 and used as the sign on to correlate the particular transmitter with a particular patient. In addition or alternatively, for example, users can have a login name and password, and a variety of different encryption algorithms can be used in the authentication process.

Other services 318 can include a number of other services that seek access to patient data. In some embodiments, other services 318 include computer-based data services such as databases, data management programs, and/or portals to interface with a user or computer accessing the data. As an example, a doctor 320 using a computing device like a personal computer, smartphone, tablet, etc. can request access through other services 318 to patient data stored by services server(s) 300. For example, the doctor might request recent and past glucose levels to analyze whether insulin injection dosages should change, and to track patient progress between doctor's office visits. The other services 318, in one embodiment, receive real-time data through services server 300 for a period of time, e.g., the past thirty days. Other services 318 can synchronize data and save data periodically through the services server(s) 300. For example, some other applications can request data hourly, others daily, and others weekly to have the data from services server(s) 300. For example, other services 318 can include applications that request data to perform data analytics, both for individual patients and for classes of patients. When other services 318 request data beyond the age range stored by services server(s) 300, that request is sent to and processed by back-end server(s) 306, which stores longer-term archived bulk and real-time data. The timing as to when various components of the system can request access to bulk and real-time data can vary. For example, the cloud computing architecture 106 can restrict other services 318 to only accessing data once per day, allowing full access at any time, or on a variety of other timeframes.

It will be appreciated that other embodiments of the cloud computing architecture 106 of FIG. 3 can include fewer or additional components. In addition, the system in accordance with embodiments of the cloud computing architecture 106 can include a plurality of cloud computing architectures so that fewer than all of the displays transmit data to a single cloud computing architecture. For example, a plurality of connected cloud computing architectures can be used throughout different geographical regions, although other arrangements are also possible to distribute the computing load.

Figure 4:
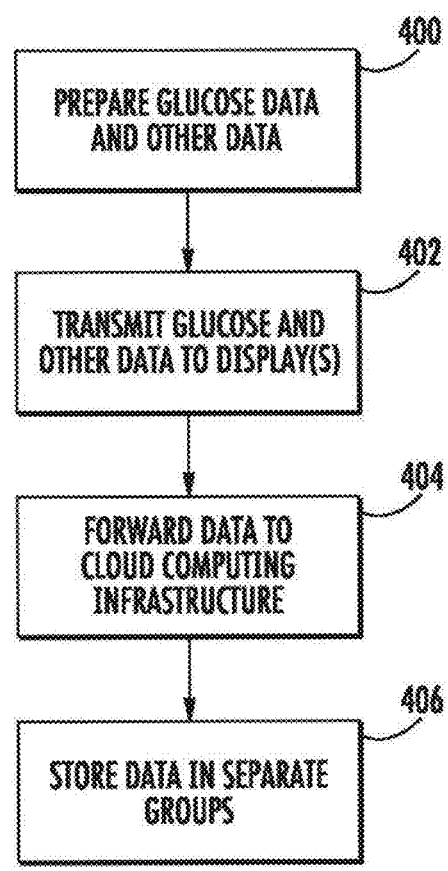
FIG. 4 illustrates an exemplary method for storing data in separate groups.

Reference will now turn to FIG. 4, which illustrates a method for storing data in separate groups. In some implementations, the continuous glucose sensor units 100 and displays 104 can create and transmit different types of data (e.g., real-time and bulk data, private and public data) that may need to be handled differently. In particular, all of the data may not be appropriate for retransmission to third-parties or other system components, such as data that contains proprietary information about system operation and data that can be used to identify a patient. Separating the data so that it can be handled differently, including different storage locations, different policies for controlling access to the data, and different storage durations can present a challenge. The data can include data relating to glucose levels, data about functioning of the system, user interaction with the system, and other types of data.

At process 400, the continuous glucose sensor unit 100 prepares data including glucose levels and other data for transmission. The data includes, for example, measured glucose values and diagnostic data. The data can include a first set of data (e.g., real-time data) and a second set of data (e.g., bulk data). Real-time data can include one or more of glucose values, a current status of a continuous glucose sensor, timestamps associated with measurements used to obtain the glucose values, and the like. Bulk data can include one or more of information for calibrating the continuous glucose sensor unit 100, information used for technical support of the continuous glucose sensor unit 100, and the like. For example, information for calibrating the continuous glucose sensor unit 100 can include the previously discussed values sampled by a patient when using a test kit. In some implementations, the electronics unit (e.g., transmitter 102) of the continuous glucose sensor unit 100 prepares the data by aggregating and/or formatting the data into form(s) or groups to be transmitted. For example, as described in more detail below, the continuous glucose sensor unit 100 can encrypt some or all of the data. In some implementations, the data is prepared in a manner corresponding to the sets of data, e.g., the real-time data and the bulk data, which can be prepared differently for the different sets of data.

At process 402, the continuous glucose sensor unit 100 transmits the glucose data and other data to one or more displays 104, some of which may be encrypted. In some of the embodiments, each of the displays 104 can store a decryption key to decrypt some, but not all, of the encrypted data to control access by a patient to certain types of data. For example, the displays 104 can decrypt real-time data including glucose levels, from which the displays 104 can generate and display a graph including the current and past glucose levels over a period of time, such as the most recent hour, six hours, or day. In some of the embodiments, the display 104 does not have a key to decrypt bulk data, such as system diagnostic information and/or raw data values in order to keep that data confidential.

At process 404, the one or more displays 104 forward the data to the cloud computing architecture 106, also referred to as cloud computing infrastructure or cloud infrastructure. Process 404 may, in some embodiments, occur automatically without a request from the user, e.g., either as data is received or at predetermined times. The displays can send different types of data to the cloud computing architecture 106 at different times. In addition, the display 104 can add more data to the data received from the continuous glucose sensor unit 100 and automatically forward the additional data to the cloud computing architecture 106. Such additional data can include, for example, the times of alarms, the time data was viewed on a display, data that is further processed by the display 104, and the like.

At process 406, the cloud computing architecture 106 stores the data in separate groups. In some implementations, for example, the shared services server(s) 304 can store real-time data and back-end server(s) 306 can store the bulk data. Various components of the cloud computing architecture 106 can store decryption keys for both groups of data to restrict access to certain data types. For example, back-end server(s) 306 can store decryption keys for both real-time and bulk data, so technical support (e.g., technical support unit 314) can access both types of data. However, other services 318 may not store a decryption key for bulk data such that it cannot be accessed through other services 318. As a result, the cloud computing architecture 106 selectively determines whether to grant access to the various categories (e.g., first set and the second set) of data by the category of data and the one or more requesting systems trying to access the data. For example, in some embodiments, the cloud computing architecture 106 can comprise a table that identifies the requesting systems. A request for data received by the cloud computing architecture 106 can identify the system making the request such that the requesting system can only access certain categories of data.

Figure 5:
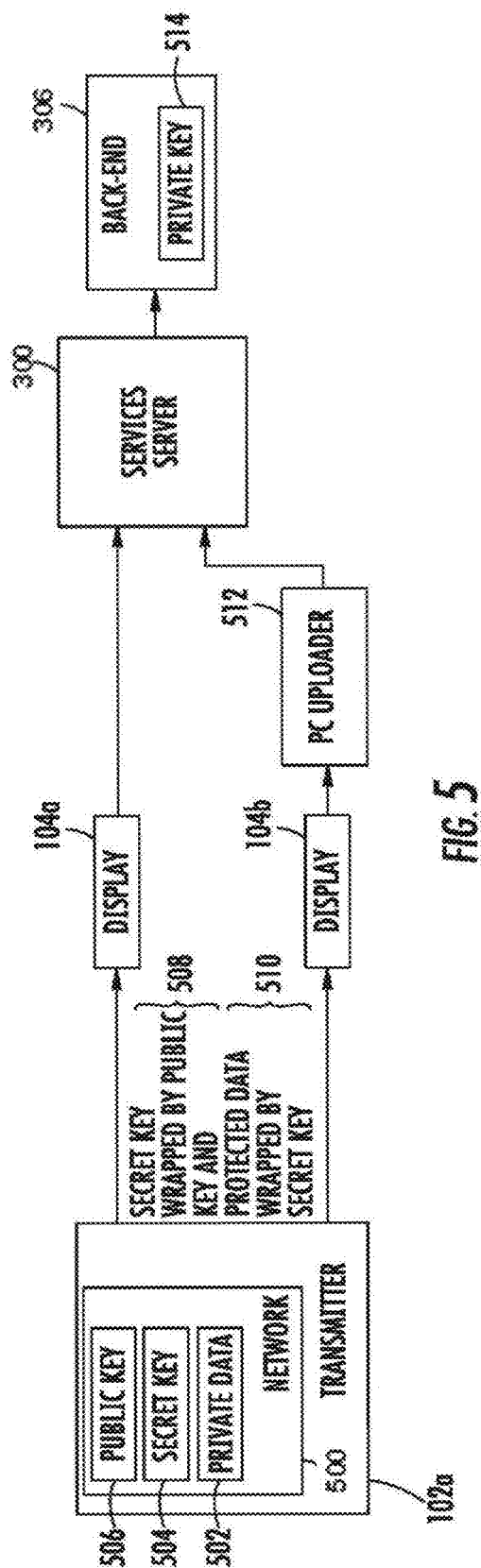
FIG. 5 illustrates an exemplary system for encrypting medical data.
Figure 6:
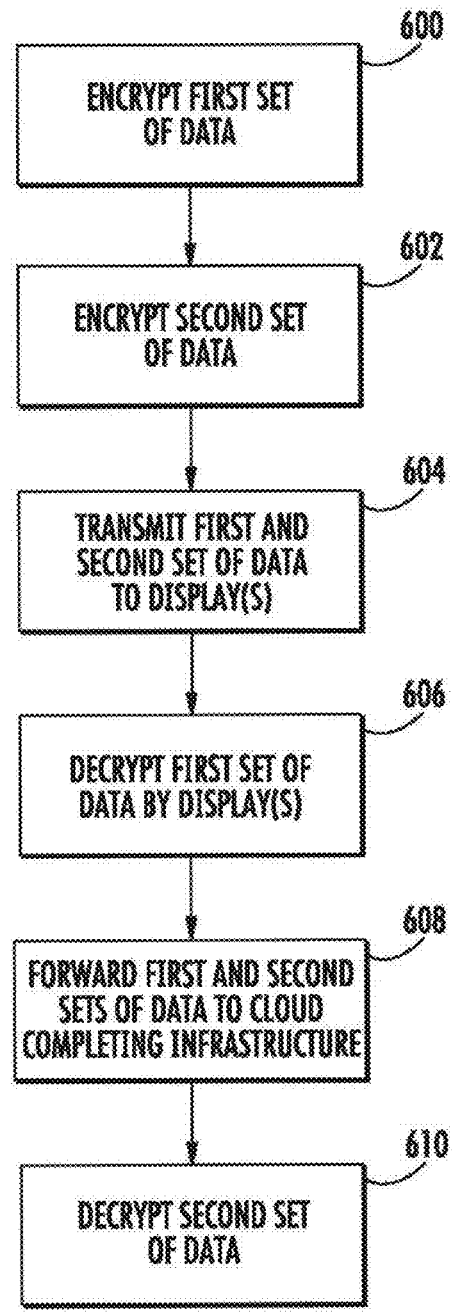
FIG. 6 illustrates an exemplary method for encrypting medical data.

Reference will now turn to FIGS. 5 and 6, which illustrate example embodiments of an encryption system and method for encrypting data, respectively. FIGS. 5 and 6 provide techniques to protect sensitive data from unauthorized access by third parties. A challenge in the art is the ability to distribute data to entities that are only authorized to receive a subset of the data. For example, the cloud computing architecture 106 can grant a service access to data that does not identify a patient, but deny the service access to patient-identifying or system diagnostic data. At the same time, the cloud computing architecture 106 can allow other entities, such as technical support, full access to system diagnostic data but not always patient-identifying data. The varying levels of security and authorization can use techniques, such as those in exemplary FIGS. 4 and 5, for controlling access to data by system components.

Conceptually, the system of FIG. 5 places a message inside a box that is locked at the transmitter 102. Only the intended recipient, such as the services server(s) 300 and/or back-end server(s) 306, has the key. In some implementations, the transmitter 102 sends the message to the display 104, such as a smartphone or dedicated receiver, which sends the encrypted message on to the services server(s) 300. The display 104 acts as a pass-through without the ability to decrypt all of the data.

In particular, transmitter 102a includes memory 500, which can be any type of nonvolatile memory that can store a public key 506, a secret key 504, and private data 502. The public key 506 is a public encryption key, such as a key for RSA 1024 encryption. The secret key 504 is an additional private key used for another level of encryption, such as the advanced encryption standard. The private data 502 can include, for example, the bulk data previously described. The secret key 504 can be stored on the transmitter 102a during the manufacturing process.

The transmitter 102a sends the secret key 504 wrapped by the public key 506 to each of the displays 104a, 104b, as illustrated at 508, and also the protected data wrapped by the secret key 504, as illustrated at 510. The displays 104a, 104b do not have the public key 506, so they cannot access the secret key 504 or use the secret key 504 to access the private data 502. Instead, the private data 502 includes data that passes through the displays 104a, 104b for transmission to the services server(s) 300 for decryption. In this manner, the displays 104a, 104b are restricted from accessing certain private data, while the cloud computing architecture 106 can access that data. In particular, back-end 306 stores the private key as shown at 514.

Although not illustrated, and as described below, the transmitter 102 also transmits other data that the displays 104a, 104b can decrypt and display to a user. This data includes, for example, real-time data and can be encrypted according to Bluetooth encryption schemes and other techniques. Display 104b can be connected to a PC uploader program 512, which can execute on a personal computer, tablet, or other computing device.

With reference to FIG. 6, a corresponding method for encrypting and transmitting data, e.g., implementable by devices and a cloud computing system architecture in accordance with the present technology, will be described. At process 600, the transmitter 102 encrypts a first set of data. For example, the transmitter 102 encrypts real-time data including glucose values using Bluetooth encryption. At process 602, the transmitter 102 encrypts a second set of data, such as bulk data that includes proprietary information that should not be accessible by the displays 104. The second set of data can be encrypted using the advanced encryption standard and a variety of other techniques.

The transmitter 102 transmits the first and second sets of data to the display(s) 104 at process 604. The transmitter 102 sends the first and second sets of data either together or at different times. For example, the first set of real-time data can be sent every five minutes, while bulk data can be sent hourly. In this manner, the transmitter 102 sends the two sets of data, each encrypted using different techniques, as different data streams to the display(s) 104.

At process 606, the display(s) 104 decrypt the first set of data. The display(s) 104 presents the data to a user on a user interface, uploads the data to the cloud computing architecture 106, provides the data to other applications, and stores the data in local memory. The display(s) 104 can forward both the first and second sets of data to the cloud computing architecture 106 at process 608. Process 608 occurs automatically upon receipt of the data, periodically, or in response to a request from a user or the cloud computing architecture 106. In some implementations, each of the displays receives the first and second sets of data in different streams at different times and forwards the streams to the cloud computing architecture 106 automatically upon receipt. In this manner, the cloud computing architecture 106 receives the first and second sets of data, each encrypted differently, at different times.

At process 610, the second set of data is decrypted. In one embodiment, the second set of data, or a portion of it, can be decrypted by the cloud computing architecture 106. In another embodiment, the second set of data (or a portion of it) can be sent to another location, such as for example, an inulin provider that has a key and is able to decrypt the second set of data. Although the display(s) 104 lack the decryption key to access the second set of data, the cloud computing architecture 106 (e.g., in the shared services server(s) 300 and/or back-end server(s) 306) and/or other locations (e.g., insulin provider) include the decryption key. In some implementations, the cloud computing architecture 106 receives and decrypts the first set of data, and provides it to both local short-term storage in the cloud services server and longer-term storage in the back-end.

Figure 7:
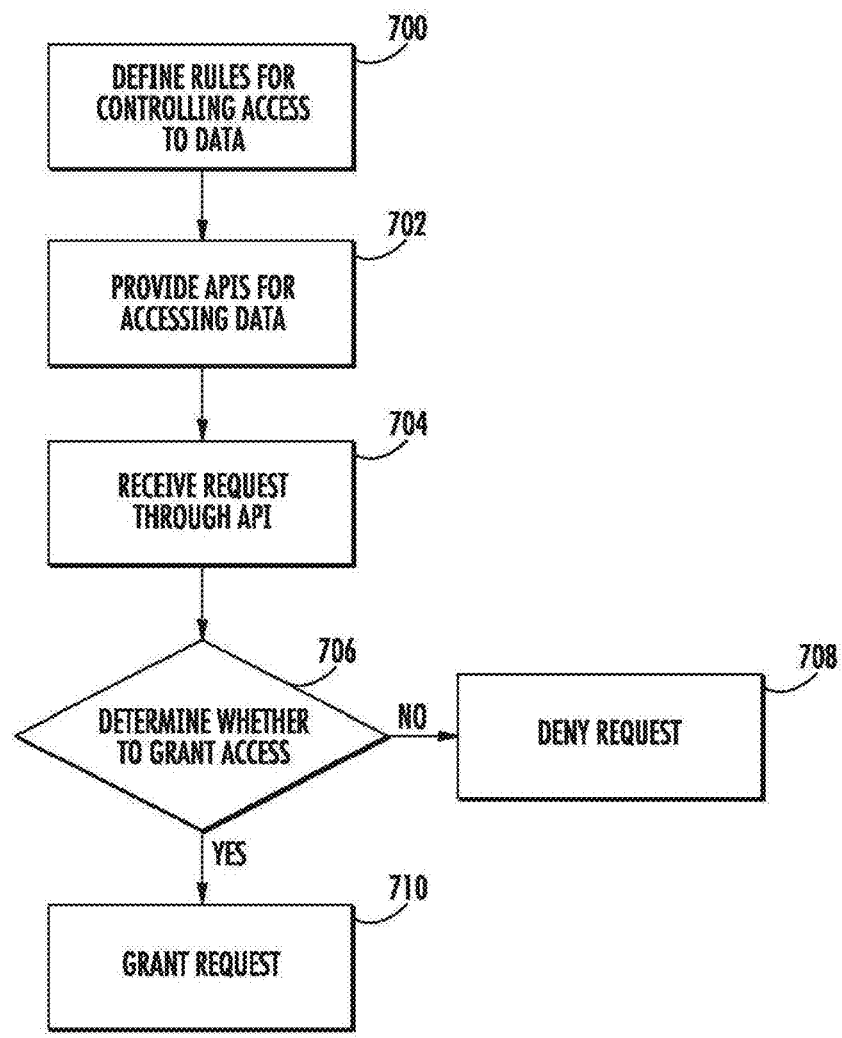
FIG. 7 illustrates an exemplary method for providing a common interface through which data can be accessed.

Reference will now turn to FIG. 7, which illustrates an exemplary method for providing a common interface through which data can be accessed. The cloud computing architecture 106 can provide an integrated system with many different components, including third-party systems. However, in some instances, this can be problematic from a regulatory standpoint, as each time a change is made to any one component, the entire systems may need to undergo regulatory review. To address this problem, for example, the cloud computing architecture 106 can be configured such that each module can be seen as being independent from a regulatory standpoint so that each module can undergo separate regulatory review. In particular, the cloud computing architecture 106 can provide a set of standard application program interfaces to provide a known format for interfacing, allowing the various components to be built and maintained separately.

Another challenge faced by the cloud computing architecture 106 is how to handle a large number of requests for access to data of different patients. For example, requests can originate from a number of different servers, computing devices, and software applications, which can have varying formats of requests and capabilities for receiving and processing responses. If the cloud computing architecture system 106 were to change to accommodate each new request and response type, the system may need to be re-certified as a medical device, which can be a timely and costly process. The method of FIG. 7 therefore provides a common interface through which to receive requests, ensuring a modular system that does not need to change for new request types.

In one example, the cloud computing architecture 106 employs a hub and spoke framework, where the hub contains rules as to what information can be accessed by each particular spoke. In this way, the spokes only have access to information that is appropriate and/or needed by that spoke. Examples of spokes include the remote monitoring application, third-party applications, and other services.

At process 700, the cloud computing architecture 106 defines rules for controlling access to data. The rules can include user permissions, approval processes for remote monitors, approval process for third parties and other software applications, and rules for controlling access from components of the cloud computing architecture 106 itself. For example, a remote monitor need not have access to proprietary bulk data, while technical support can access the bulk data. Other examples for rules include controlling the volume of data that can be accessed, controlling the timing of when data can be accessed, and others. Such rules can be implemented when the system is put in place for a user or, for example, by an administrator that has permissions and authorizations to set such rules in the cloud computing architecture 106. Such permissions and authorizations may have to be in compliance with privacy laws and regulations.

At process 702, the cloud computing architecture 106 provides a set of application program interfaces for accessing data. The application program interfaces define a standardized interface through which requests for data can be received. The standardized interfaces are provided to third-parties and application developers to create requests that adhere to the application program interface. At process 704, a computing device or application provides a request through one of the application program interfaces to the cloud computing architecture 106.

Next, at process 706, the cloud computing architecture determines whether to grant the request for access to data based on the rules defined in process 700. For example, the cloud computing architecture 106 identifies the requesting party and determines whether the requesting party should obtain access to the requested data. If, at process 706, the cloud computing architecture determines that the requesting party does not have access to the requested data, then at process 708 the cloud computing architecture 106 denies the request. If, at process 706 the cloud computing architecture 106 determined that the requesting party does have access to the requested data, than at process 710 the cloud computing architecture 106 grants the request. Processes 704-710 can be performed by a number of different components within the cloud computing architecture. For example, requests for recent data can flow though the services server(s) 300, while requests for older archived data can be processed by back-end server(s) 306.

Figure 8:
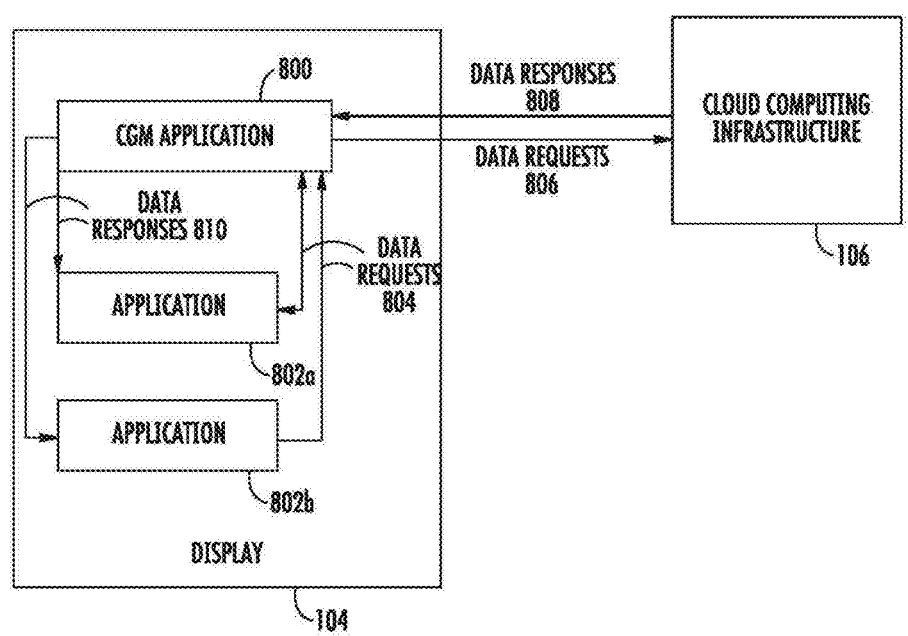
FIG. 8 illustrates an exemplary system diagram of handling requests from a display to the cloud computing architecture.

FIGS. 8 and 9A-9D illustrate exemplary method and system diagrams in accordance with embodiments of the disclosed technology for handling requests from a computing device such as display 104 to the cloud computing architecture 106. As discussed above, handling requests from a number of different servers and applications can present challenges to the cloud computing architecture 106. One solution is to provide common application program interfaces at the cloud computing architecture 106, as described in FIG. 7. Another solution includes placing requests in a common format using an application (app) executing on the display 104. FIGS. 8 and 9 provide an example of placing a request in a common format using an application executing on the display 104.

Referring to FIG. 8, display 104 includes a continuous glucose monitor application 800 and a plurality of other applications 802a, 802b. The continuous glucose monitor (CGM) application 800 can be an application designed to interface both with transmitter 102 of the continuous glucose sensor unit 100 and the cloud computing architecture 106. Applications 802a, 802b provide data requests 804 to the CGM application 800, which can include rules logic as described above in relation to FIG. 7 to determine whether the data request should be granted for the requesting application 802a, 802b.

If the request should be granted and the data is stored locally, the CGM application 800 provides the data response as shown at 810. In some embodiments, the CGM application 800 forwards the data requests 806 to the cloud computing architecture 106, which determines whether to grant the request using the techniques described in FIG. 7. If the request should be granted, the cloud computing architecture 106 sends the data responses 808 to the CGM application 800, which forwards the data responses 810 on to the requesting application 802a or 802b.

Figure 9A:
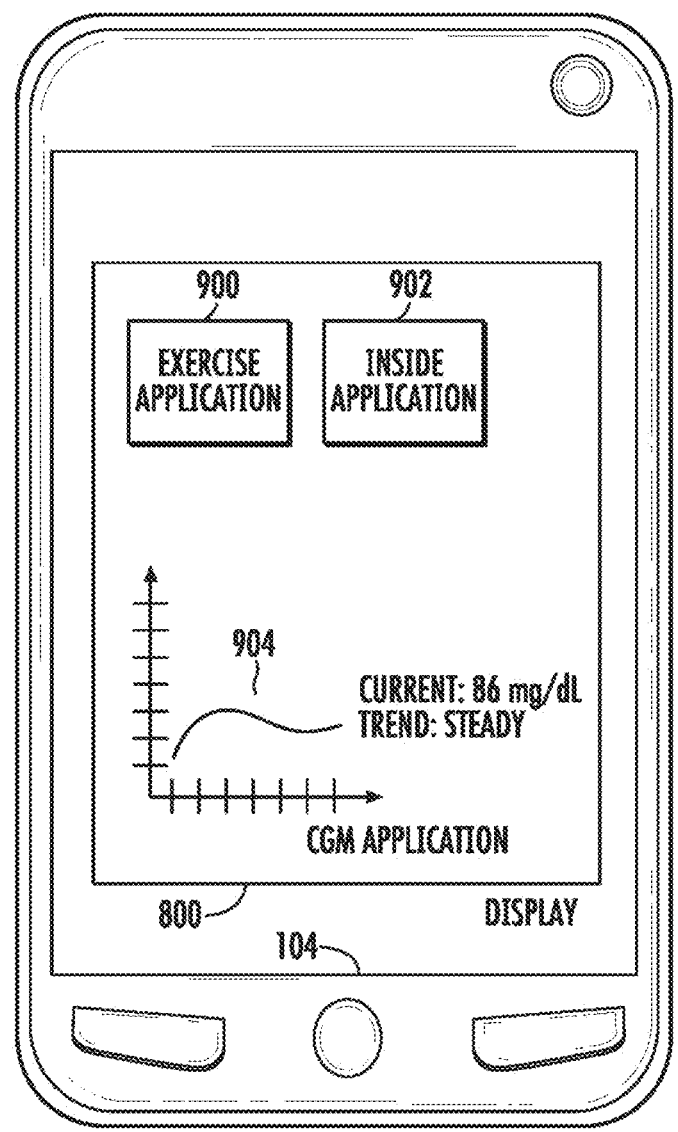
FIG. 9A illustrates an example of continuous glucose monitor application executing on a display.

FIG. 9A illustrates an exemplary embodiment of a user interface of CGM application 800 executing on display 104. The CGM application 800 displays, at 904, information relating to glucose levels including a chart of recent glucose levels, a current glucose level (e.g., 86 mg/dL, and a trending pattern (e.g., rising, steady, or dropping)). In some implementations, the CGM application 800 displays icons 900, 902 as links to other applications, such as applications 802a, 802b described in FIG. 8. In this example, the icon 900 links to an exercise application, and the icon 902 links to an insulin application. These links within the CGM application 800 allow a user to log into multiple applications using a single login, as described above regarding single sign on 312 in FIG. 3. In addition, the links can provide a convenient way for users to access other information stored by different applications, whether from the same or a different manufacturer, which are relevant to glucose levels and trends.

Figure 9B:
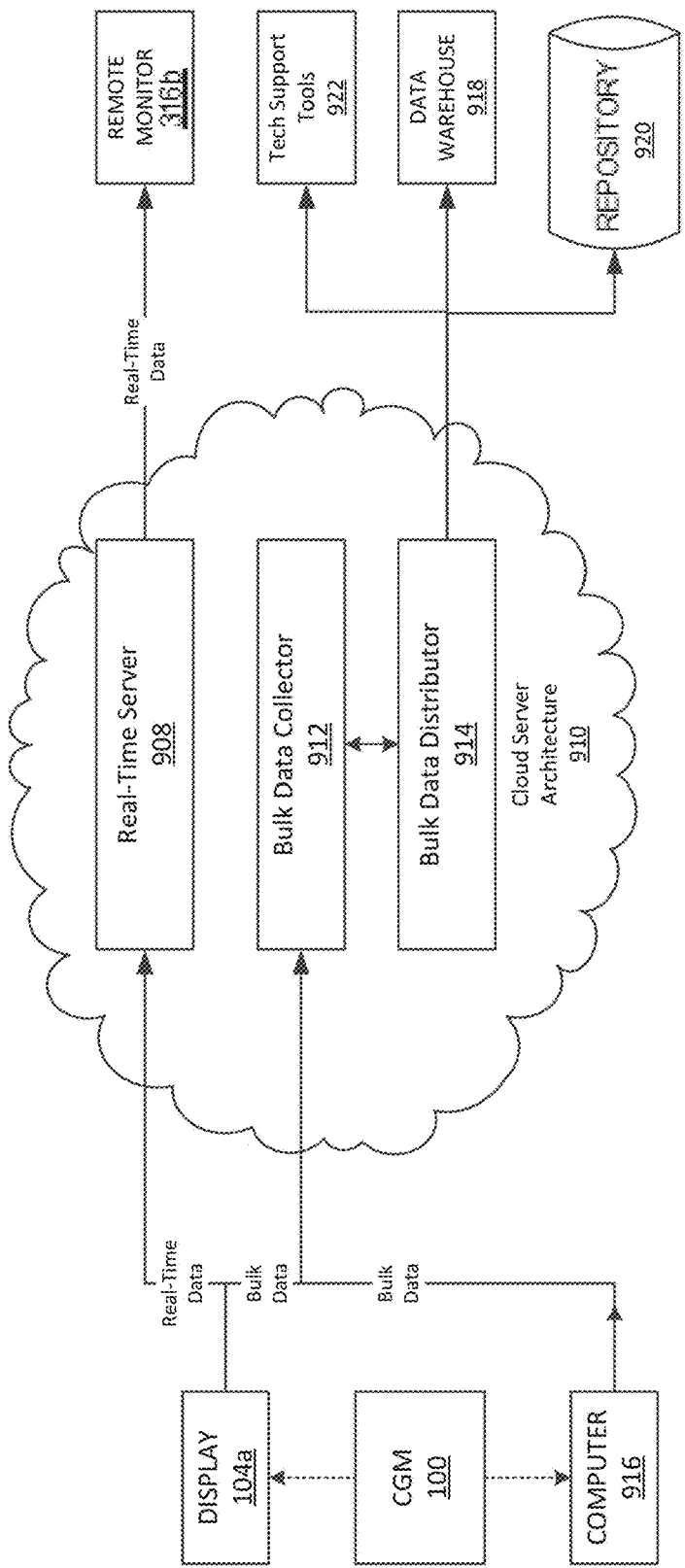
FIG. 9B illustrates an exemplary embodiment of a system in accordance with cloud-server architecture for performing aspects of the described technology.
Figure 9C:
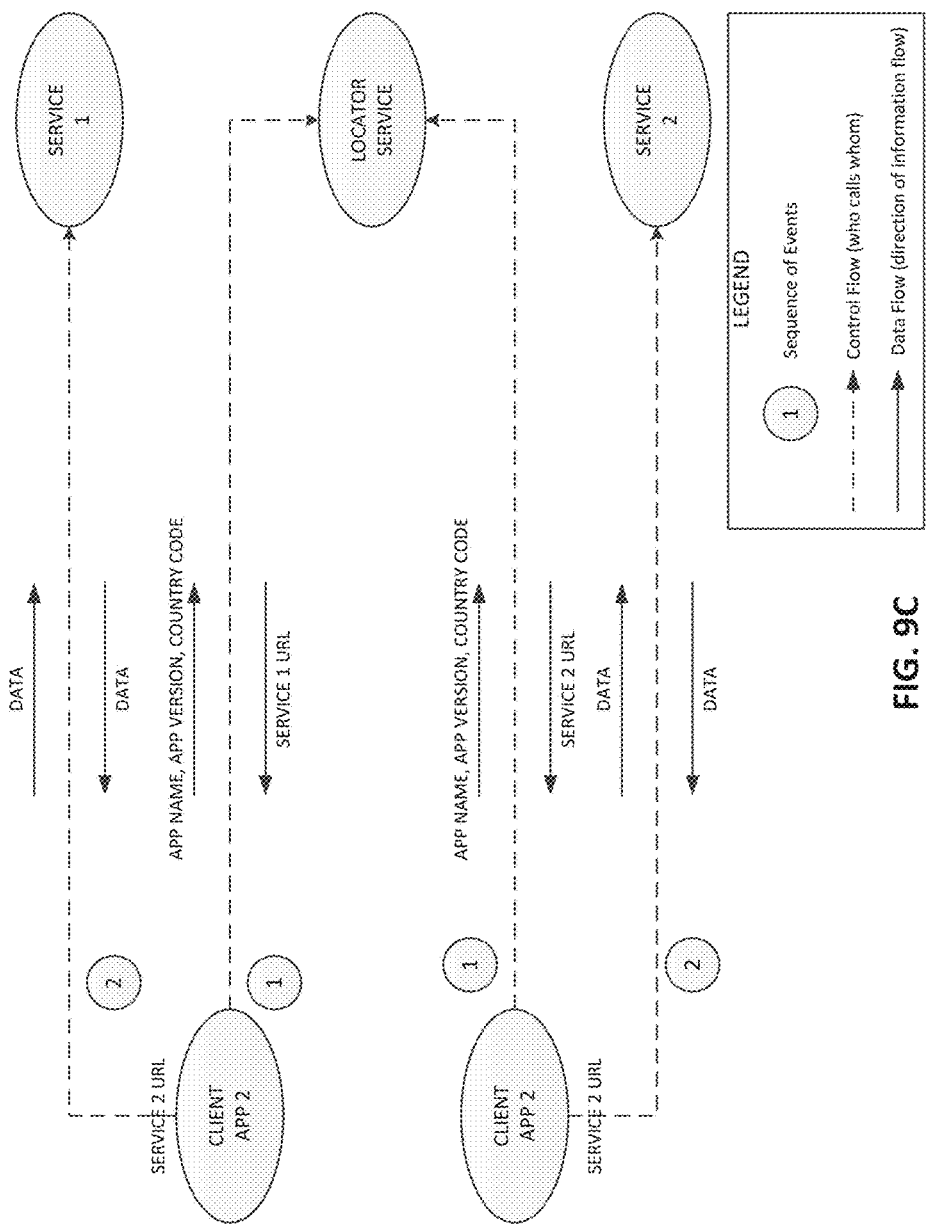
FIG. 9C illustrates data and control flows associated with an exemplary locator service.

FIG. 9B illustrates an exemplary embodiment of a system in accordance with cloud-server architecture 106 for performing aspects of the described technology. In this illustration, display 104a comprises a smartphone executing an application such as CGM application 800 described in relation to FIG. 8. In other instances, display 104a may be a computing device such as a laptop computer, desktop computer, tablet, PDA, wearable computing device, and the like. For example, display 104a is in communication with continuous glucose sensor unit 100. The display 104a may be communicating wirelessly with continuous glucose sensor unit 100, or it may be connected to the continuous glucose sensor unit 100 through a wire or optical cable.

The display 104a can receive a plurality of types of data from continuous glucose sensor unit 100 and transmit the plurality of types of data to cloud server architecture 910, an example embodiment of the cloud computing architecture 106. Data transmitted from the display 104a to the cloud server architecture 910 may be transmitted at different time periods based on a classification assigned to the data. Data may be classified as real-time data and bulk data. Real-time data may be transmitted from the display 104a to the cloud server architecture 910 at a higher frequency such as once every minute, once every five minutes, once every 10 minutes, etc., while bulk data may be transmitted from the display 104a to the cloud server architecture 910 at a relative lower frequency than the real-time data such as once every 30 minutes, once every hour, once every two hours, etc.

For real-time information, data transmitted from the continuous glucose sensor unit 100 is received by the display 104a and transmitted to a real-time server 908 that is included as part of the cloud-server architecture 910. The real-time information includes one or more of estimated glucose value(s) (EGV), glucose concentration rate of change information, CGM alert information, raw sensor data, and/or other type of public or private data discussed herein. Real-time data is separated from bulk data because action may need to be taken based on the real-time data in an immediate or timely manner. Further, the real-time server 908 is configured to handle a large amount of real-time data on a rapid basis. For example, a glucose monitoring system may have up to 150,000 or more users and each user may transmit up to 288 values per day from the respective user's display 104a to the real-time server 908.

Because of the volume and frequency of data that must be managed by the real-time server 908, in some instances a locator service may be used. Data and control flows associated with an exemplary locator service are show in in FIG. 9C. At the beginning of an application session, the client application executing on a smartphone, e.g., such as the CGM application 800 as described above, calls the locator service (running, for example, on real-time server 908) and receives a URL that it uses for subsequent calls. The input parameters typically include the application name, application version and a country code. The locator service uses the parameters to determine where to go (hence the term locator) for all other services. This approach provides the ability for the real-time server 908 to scale out without requiring the application to be changed; and the ability for the server to provide different service implementations for different app revisions or countries. Existing applications that do not use the locator service still continue to work. The locator service includes logic to determine where to send app requests in a dynamic manner.

With reference again to FIG. 9B, information can be transmitted from the real-time server 908 to a remote monitor 316b using various mechanisms. The remote monitor 316b can be a device such as a smartphone executing an application (app) such as a remote monitoring app that is designed to display to the remote monitor user at least some data associated with the glucose data from CGM application 800 described in relation to FIG. 8. For example, in one instance at least a portion, if not all, of the real-time information is pushed from the real-time server 908 to one or more remote monitors 316b. The real-time information may be delivered on a periodic basis to the remote monitors 316b such as once every 30 seconds, once every minute, once every two minutes, once every five minutes, once every 10 minutes, etc. In some implementations, the real-time server 908 can monitor the real-time information for trends and tendencies, and make the remote monitors 316b aware of such trends. When data is pushed to the remote monitor 316b, it may require that the remote monitoring application on the device 316b be open and running. If the remote monitoring application is not open and running on the remote monitor 316b, then the data is queued at the real-time server 908. In some implementations, once the remote monitoring application is opened on the remote monitor 316b, the data is automatically pushed to the remote monitor 316b. In some implementations, once the remote monitoring application is opened on the remote monitor 316b, the user is notified of awaiting data. Using the remote monitoring application, for example, the remote monitor user may then request the data to be transmitted from the real-time server 908 to the remote monitor 316b. In some implementations, if the remote monitoring application is not open and running on the remote monitor 316b, a notification such as a text message (e.g., SMS or MMS) is sent from the real-time server 908 to the remote monitor 316b as the remote monitor 316b would not have real-time data on hand to trigger an alert on its own when the remote monitoring application is closed (in background on iPhone, for example).

In some implementations, the real-time server 908 interfaces with the remote monitoring application on the remote monitor 316b and wakes the remote monitoring application. Once the remote monitoring application wakes, it requests data from the real-time server 908.

Remote monitors 316b are allowed access to receive certain information from the real-time server 908. This is information that is related to only a defined one or more continuous glucose sensor units 100 and their respective displays 104, e.g., operating the CGM app 800. The remote monitor 316b is not allowed to access data that is not authorized. In some implementations, the remote monitor 316b can send a request to the real-time server 908 and data associated with at least one of the one or more continuous glucose sensor units 100 and respective displays 104 that the remote monitor 316b is allowed to read will be delivered to the remote monitor 316b subsequent to the request. In some implementations, the remote monitor 316b can be a smartphone. In some implementations, the real-time server 908 can comprise a Class II device as defined by the U.S. Food and Drug Administration (FDA), and data is handled in accordance with that classification.

In some embodiments, the cloud-server architecture 910 further includes bulk data collector (BDC) 912 and bulk data distributor (BDD) 914. In some embodiments, BDC 912 and BDD 914 are data processing engines operated on one or more computers, e.g., servers, in communication with one another. In some implementations, the display 104a sends bulk data (as described herein) to the BDC 912 on an intermittent basis. For example, the display 104a may send bulk data from the display 104a to the BDC 912 once every hour. In some implementations, bulk data is uploaded from the continuous glucose sensor unit 100 to a computer 916, e.g., a personal computer. At least a portion of the bulk data is then transmitted from the computer 916 to the BDC 912. Similar to above, data may be transmitted on a periodic basis from the computer 916 to the BDC 912. For example, data may be transmitted once each hour from the computer 916 to the BDC 912. The data transmitted to the BDC 912 can comprise private and public data (as described herein). In some implementations, the BDC 912 can comprise a Class II device as defined by the U.S. Food and Drug Administration (FDA) and data is handled in accordance with that classification.

As noted, the cloud-server architecture 910 also includes BDD 914. The BDD 914 provides fan-out capability for data received from the BDC 912. For example, at least a portion of the data from the BDC 912 can be provided to one or more of a technical support tool 922 and a long-term data warehouse 918. Warehoused data can include public and private data. Technical support tools 922 can include, for example, a share support tool, a repository tool, and a transmitter tool. The share support tool (a tool that provides technical support related insights for display 104a and remote monitor 316b) includes an ability to present data tables and data charts that are sent from the display 104a (automatically) and the continuous glucose sensor unit 100 (on demand by user). In some implementations, the data tables can present all data that was sent from the display 104a and continuous glucose sensor unit 100 to the data server (the real time server 908 or the bulk data collector 912), categorized by data type (e.g., EGV data, logs, etc.) and by data source (display 104a or continuous glucose sensor unit 100). In some implementations, the data charts present the data from tables chronologically in a visual form. The data sources can be identified in the chart. The repository tool supports data visualization of the display 104a and continuous glucose sensor unit 100 data, as data tables and charts. The repository tool includes support of continuous glucose sensor unit 100 data visualization. For example, when a user returns a receiver for investigation, the receiver can be downloaded using this tool to further investigate the complaint, in-house.

At least a portion of the data from the BDD 914 can be provided to a repository 920 for analysis and/or reporting. This information is generally called retrospective data. Retrospective data can generally be defined as bulk data and any real-time data that was generated in the past. For example, real-time data not generated within the last five minutes can be considered retrospective data. In some implementations, the BDD 914 can comprise a Class II device as defined by the FDA, and data is handled in accordance with that classification.

Generally, access to the data shown in FIG. 9B is controlled. For example, an authorization manager (not shown in FIG. 9B) is used to control third-party access to the BDD 914, the retrospective data 920 and the data warehouse 918. In some implementations, the authorization manager can be token based. Access to certain data can be allowed or restricted based on the token held by an accessing third party. Optionally or alternatively, a patient can provide a third-party with access to that particular patient's information. For example, an adult patient may provide a remote monitor 316b. Based on responses from the third-party, a token can be customized to the third-party's authorization. In some implementations, a third-party can access certain information (e.g., a certain patient's data) using, for example, a login through a social media website such as Google, Facebook, Twitter, etc.

Figure 9D:
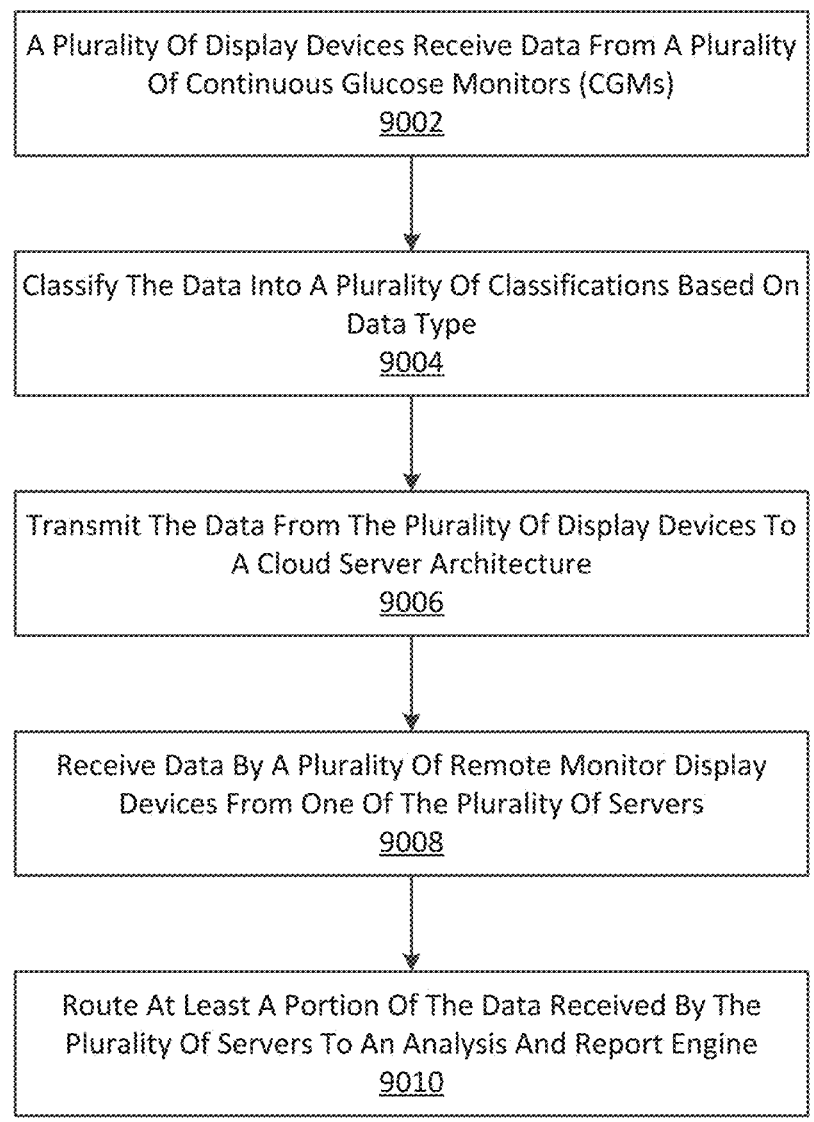
FIG. 9D is a flowchart illustrating a method for securely collecting, analyzing and reporting data related to glucose monitoring levels by a plurality of continuous glucose monitors.

FIG. 9D is a flowchart illustrating a method for securely collecting, analyzing and reporting data related to glucose monitoring levels by a plurality of continuous glucose monitors. At process 9002, data is received by a plurality of display devices (e.g., display(s) 104) from a plurality of continuous glucose monitors (CGMs), e.g., continuous glucose sensor units 100. At process 9004, the data is classified into a plurality of classifications based on data type. In some implementations, classifying the data into a plurality of classifications based on data type comprises classifying the data as real-time data and bulk data. In some implementations, the display 104 classifies the received data into the plurality of classifications based on the data type, whereas in other implementations the continuous glucose sensor unit 100 implements the process 9004 prior to the process 9002 to classify the data into the plurality of classifications based on the data type. In such implementations, the continuous glucose sensor unit 100 may classify only some of the data, in which the display 104 may classify the received unclassified data and/or reclassify the received classified data.

At process 9006, the classified data is transmitted from the plurality of display devices to a cloud server architecture in accordance with the present technology, e.g., cloud server architecture 106. The cloud server architecture 106 comprises at least a plurality of servers that receives the data from the plurality of display devices on an intermittent basis, such as the system in accordance with the cloud server architecture 910. The plurality of servers of the cloud server architecture can comprise at least a real-time server and a bulk data collector, e.g., real-time server 908 and BCC 912, respectively. In some implementations, the cloud-server architecture may further comprise a locator service, wherein the plurality of display devices connect to the cloud server architecture through the locator service. The data routed to a particular server of the plurality of servers is determined by the data type and the intermittent basis or transmission from the display device to the server can vary depending upon data type. For example, real-time data is routed to the real-time server from the plurality of display devices and the bulk data is routed to the bulk data collector from the plurality of display devices. The real-time data may be routed to the real-time server from the plurality of display devices at an intermittent basis that is more frequent that the intermittent basis that the bulk data is routed to the bulk data collector from the plurality of display devices. For example, the real-time data may be routed to the real-time server from the plurality of display devices once every five minutes and the bulk data is routed to the bulk data collector from the plurality of display devices once every hour.

At process 9008, data is received by a plurality of remote monitor display devices (e.g., remote monitor 316b) from one of the plurality of servers, e.g., real-time server 908. The data sent to each of the plurality of remote monitor display devices can depend upon the data type and upon the display device that transmitted the data to the one of the plurality of servers. In some implementations of the process 9008, the data is sent to the plurality of remote monitor display devices immediately upon receipt by the one of the plurality of servers of the cloud server architecture. Whereas in some implementations of the process 9008, the cloud server architecture (e.g., real-time server 908) processes the data according to rules associated with each remote monitor 316 and sends data in accordance with the rules to the respective remote monitor device. At process 9010, at least a portion of the data received by the plurality of servers is routed to an analysis and report engine. In some implementations of the process 9010, a BDD 914 of the cloud server architecture provides the least a portion of the data to one or more of the tech support tools 922, data warehouse 918, and/or repository 920. The data is analyzed and reports generated by the analysis and report engine.

Backfilling

Figure 10:
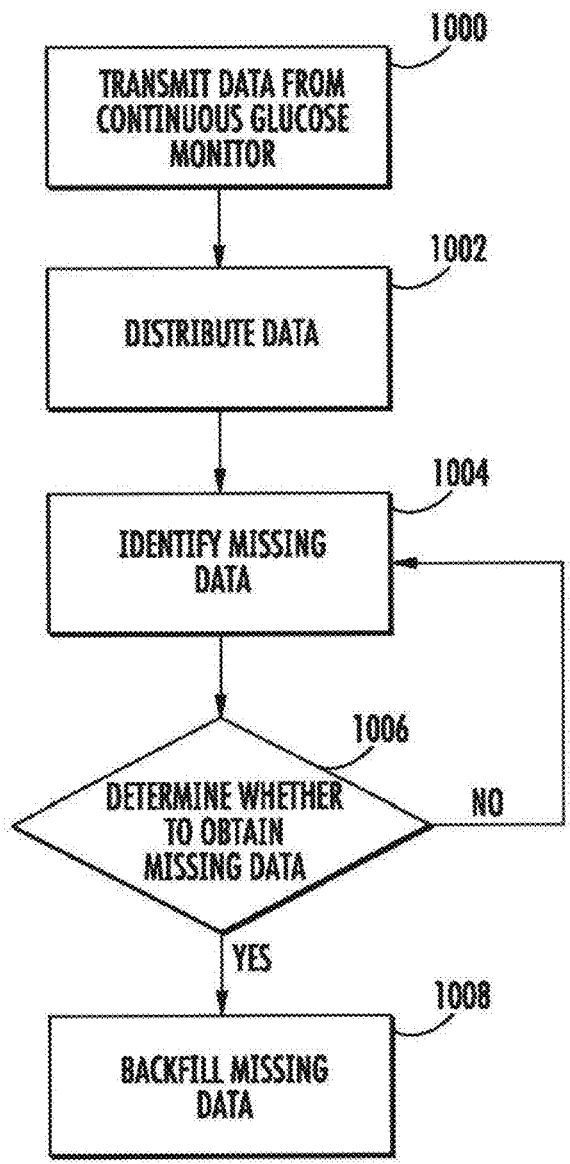
FIG. 10 illustrates an exemplary method for backfilling missed data.
Figure 11:
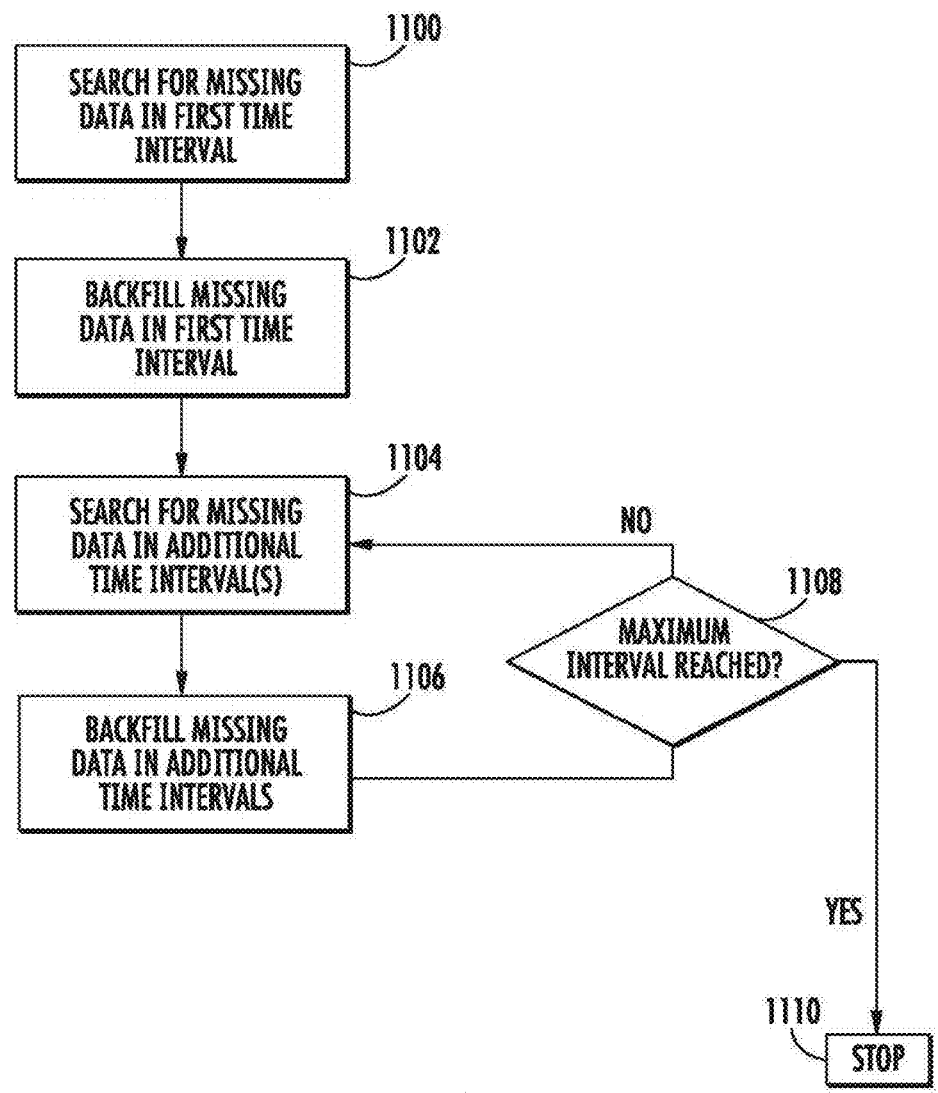
FIG. 11 illustrates an exemplary method for backfilling missed data.

FIG. 10 illustrates an exemplary method for backfilling data. One challenge that can occur when providing data to multiple displays and a distributed cloud computing architecture is ensuring that each application or device includes up-to date data. For example, a user can turn off an application, such as the CGM application 800, such that the application executing on the display device (e.g., display 104) will not receive data. Or, the display might be turned off. Even if the display is on and receives the data, it might be turned off or disconnected from the network when it normally would forward the data to the cloud computing architecture. If an application or device does not receive data, it will not be up to date. FIGS. 10 and 11 describe exemplary methods that allow data to be backfilled into an application to bring the application up to date. Up to date can mean that the application or server has all data available to it.

Additional challenges arise with the use of multiple data streams throughout the system as described herein. For example, a real-time and a bulk data stream can be separately sent to a plurality of displays 104 by continuous glucose sensor units 100, which forward those data streams on to a cloud computing architecture 106. The cloud computing architecture 106 can receive, and separately store, multiple copies of data streams from different displays connected to a common continuous glucose monitor. For example, there may also be some differences in the data streams depending on which display forwards the data to the cloud computing architecture 106 due to different calibration values and the ability of the displays to add their own additional data to the data streams.

Figure 12A:
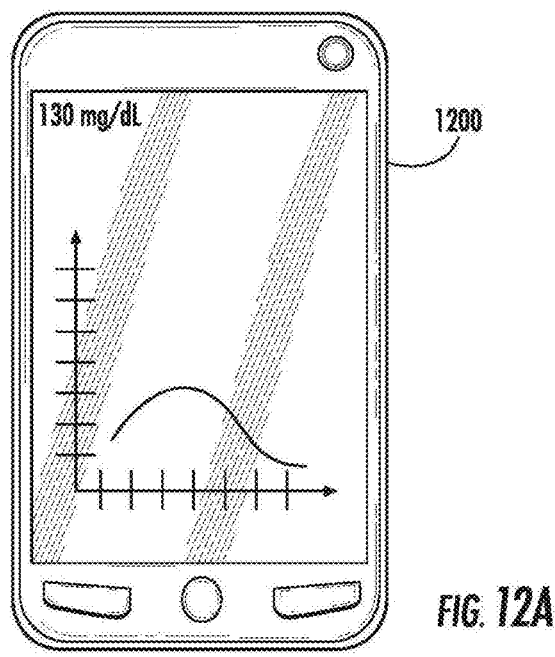
FIGS. 12A and 12B illustrate various views dependent upon the orientation of the display.
Figure 12B:
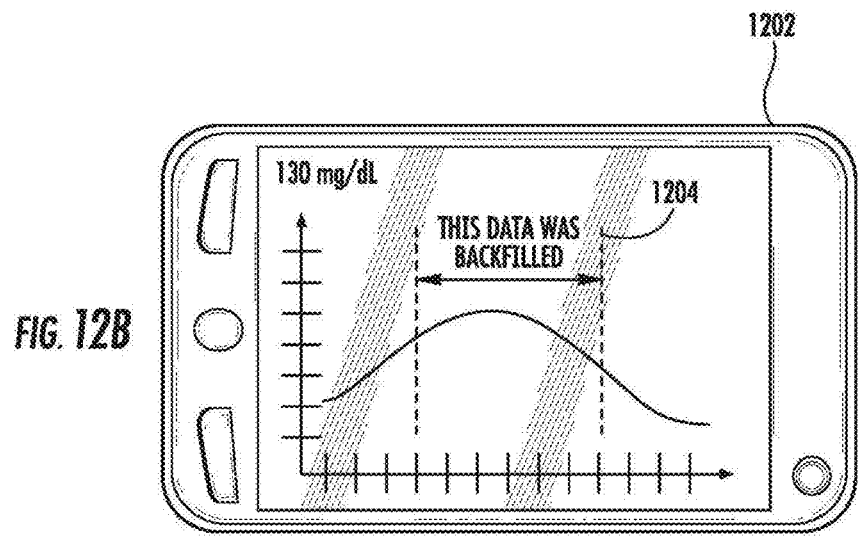

Another challenge can arise with the user being able to distinguish whether data was obtained as it was scheduled to be received ("as-scheduled data") or as part of a backfill process. Accordingly, the user interface may display the data differently depending on whether it was obtained as scheduled or backfilled. For example, backfilled data can be displayed differently. In one non-limiting example, as shown in FIG. 12B, backfilled data can be shown by using a dashed line 1204 on the line indicating glucose levels. Other ways of showing backfilled data as distinguished from as-scheduled data is using different color line segments for the backfilled data and the as-scheduled data. Referring to FIGS. 12A and 12B, in some embodiments, the display 104 may have an orientation sensor such as are available in smartphones so that while in portrait view 1200, the backfilled data points are displayed the same as real-time data points, but when the display is oriented in the landscape mode 1202, backfilled data can be displayed differently. For example, a synopsis or condensed version of the data may be displayed in the portrait view 1200, but when oriented in the landscape mode 1202, additional details can be displayed.

Returning to FIG. 10, at process 1000, a continuous glucose monitor (e.g., continuous glucose sensor unit 100) transmits data. The data can include both real-time and bulk data, which can be encrypted as described previously. The glucose values can be time stamped to track when the continuous glucose monitor sampled the glucose level and facilitate checks to make sure that various system components include a complete data set with all glucose samples.

In some implementations, the continuous glucose monitor transmits data periodically, such as every five minutes, allowing the monitor and associated transmitter to be placed in a low-power state to conserve battery life. In other implementations, the continuous glucose monitor transmits data at intervals other than five minutes. Both real-time and bulk data can be transmitted at each period, or real-time data can be transmitted every five minutes while bulk data is transmitted less frequently, such as hourly.

Next, at process 1002, the display device(s) in communication with the continuous glucose monitor, such as display(s) 104, distribute the received data, which can include both real-time and bulk data. The display(s) distribute the data to the cloud computing architecture 106, which can include both short-term storage (e.g., up to thirty days) such as in services server 300 and longer-term storage such as in back-end server 306. The displays can distribute the real-time and bulk data to the cloud computing architecture 106 as separate data streams.

Next, at process 1004, components of the data communication ecosystem in accordance with the present technology can identify missing data. Because the data streams are distributed throughout the system, it is possible that one or more components that should have received the data upon distribution did not. For example, a display may be out of wireless range from a continuous glucose monitor, or a network connection within the cloud computing architecture can be down. In some implementations, computing devices, such as servers in the cloud infrastructure, might be down or undergoing maintenance and therefore do not receive the data as it is distributed.

The various components of the system can determine whether any data is missing. For example, the display 104 itself can determine whether it is missing any real-time data by examining the timestamps associated with glucose values or other markers indicating an order of data (e.g., each glucose value is associated with a consecutively numbered value). If there is a gap in the timestamps or other marker, such as when a glucose value was not received for fifteen minutes despite expecting glucose values from the continuous glucose sensor unit 100 every five minutes, the display 104 identifies the data as missing. Similarly, the cloud computing architecture 106, e.g., including the services server(s) 300 and back-end server(s) 306, can determine whether any data is missing by examining timestamps or other marker. In addition, for example, third-party applications can determine if any data is missing. In some implementations, the data synchronization server 302 can determine if any display 104, the services server(s) 300, or the back-end server(s) 306 is missing data. In this way, it can be determined by the cloud computing architecture 106 whether each component having missed data should backfill the missed data.

At process 1006, the component that identified it was missing data determines whether to obtain the missing data. There can be a maximum amount of time during which to backfill data. For example, data that was missing from more than six hours previously might not be backfilled into display 104 that missed a large number of transmissions from the continuous glucose sensor unit 100. Other components of the system, such as the back-end server(s) 306, can backfill all missing data without time limitations, in some implementations. Similarly, components of the ecosystem such as the display 104 may only backfill some categories of data after a certain time period has elapsed (e.g., six hours) while not backfilling other types. Furthermore, the backfill period may be less than the period for which data may not have been available. For example, bulk data may be backfilled even after a six hour window where data was missed, while real-time data may not be. Furthermore, the backfill period may be less than the period for which data may not have been available. For example, data may not have been available to a display for the past six hours, but when data becomes available, the display may only backfill the last two hours rather than all six hours of missed data. In another example, although display 104 may be missing for an extended period (e.g. six hours), the display may only backfill a subset of that time (e.g., two hours) during a given period of time in order to preserve resources (e.g., battery life) of components of the system. Determining whether to backfill data may be done because after a certain amount of time, some of the data may become stale to certain components of the system, backfilling may consume too much battery power of one or more components of the system (e.g., transmitter 102), and/or a component of the system (e.g., display 104) requesting the backfilled data may only be configured to display a certain range of data, such as the last six hours, making backfilling further than the range possibly unneeded. Computational and storage needs may also be decreased by only selectively backfilling data.

If the component determines that it should not obtain the missing data, the method of FIG. 10 can return to identify any additional missing data. For example, display 104 can determine that it missed data for a period of ten straight hours. In this example, it may determine to not obtain data older than six hours previously, or the transmitter 102 of the continuous glucose sensor unit 100 may have only stored the past six hours of data, and return to identify further missing data within the last six hours at process 1004.

If the missing data should be obtained, at process 1008 the component backfills the missing data. In some implementations, the component backfills from the oldest available data (or the oldest time period desired) to the most recent time period. In other implementations, the component backfills from the most recent data to the oldest. The process of backfilling missing data can occur with respect to an individual stream, such as real-time or bulk data, or both streams. As examples, display 104 can request missing data either from the continuous glucose sensor unit 100 or from services server(s) 300. Services server(s) 300 can also be missing data, and it can, in some implementations, receive, for example, four data streams associated with a single continuous glucose sensor unit 100. The continuous glucose sensor unit 100 sends a real-time data stream and a bulk data stream to each connected display, such as two displays, resulting in four streams. The services server(s) 300, and other components in the cloud computing architecture 106 such as back-end server(s) 306, can store an indication not only of the continuous glucose sensor unit 100 that sent the data, but also which display sent the data. In this manner, the components of the cloud computing architecture 106 can store separate data streams (e.g., real-time and bulk) on a per-display basis. This helps with troubleshooting technical support issues by back-end server(s) 306. When a system component obtains backfilled data, the system component also stores an indication that the data was backfilled rather than received upon at initial distribution. This also assists with diagnosing problems, such as when an alarm is missed as previously described.

In addition, storing multiple data streams from multiple displays associated with a single continuous glucose sensor unit 100 allows the cloud computing architecture 106 to validate the data streams against each other. For example, the real-time data stream from a first display can be compared to the real-time data stream from a second display and any differences noted. Differences could indicate that the two displays are not using the same calibration values or other system issues. Detecting any differences can result in a prompt to the user on either display, such as a prompt to the user to update the calibration values. Comparing the two streams also allows confirmation that the data is being effectively captured by both displays.

FIG. 11 illustrates another exemplary method for backfilling missed data. In some situations, the amount of data to backfill should be limited. For example, a user may turn their display 104 off (e.g., turn smartphone off) for an extended period of time or even replace their smartphone. However, when a user has had their continuous glucose monitor (e.g., continuous glucose sensor unit 100) for an extended period of time, backfilling all prior data can cause system congestion and is unnecessary. As a result, the method of FIG. 11 searches for any missing data within defined time intervals up to a maximum amount of time such as, for example, one day, 12 hours, six hours, one hour, 30 minutes, ten minutes, five minutes, one minute, etc.

At process 1100, a system component searches for missing data in a first time interval. As described above, any system component, such as display 104, services server(s) 300, back-end server(s) 306, a remote monitor display such as 316, or other component can search for any missing data. The first time interval can vary based on the device searching for missing data. For example, a user's computing device such as display 104 may have relatively limited amounts of memory compared to a server. The display 104 might search to backfill missing data in an interval of six hours, up to a maximum of twenty-four hours, whereas a services server 300 can search for missing data going back over the most recent thirty days. In some implementations, display 104 may automatically send backfill data once it has received it; however, the display may need to request data from the transmitter 102 of the continuous glucose sensor unit 100. This may be because the transmitter 102 may have a more limited power source (e.g., a battery) than does the display 104. At process 1102, the system component backfills any missing data discovered during the first time interval as described above.

Next, at process 1104, the system component searches for missing data in additional time intervals. Continuing the example above, display 104 can search for missing data in the past six hours and backfill any missing data by requesting it from the continuous glucose sensor unit 100. Next, the display searches for missing data in an additional time interval—such as another six hours. Of course, other time intervals can also be used. The most recent time interval can be the first to backfill data beginning most recently in time, or the search can begin at the maximum past duration and search towards newer data that might have been missed. At process 1106, the component backfills any missing data from the additional time interval.

At process 1108, the system component determines if the maximum interval has been reached. For example, if display 104 has already searched over the most-recent twenty-four hours, it will stop searching at process 1110. If, however, additional time intervals exist up to the maximum interval for a particular component to search, process 1104 repeats to continue searching for data that should be backfilled.

In addition, the backfilling techniques disclosed herein are applicable to a variety of system components and applications. One challenge that can arise is providing and backfilling data to remote monitoring applications or remote monitor devices. The real-time data can go to remote monitor devices, but a remote monitor device may be offline or out of wireless range. A remote monitor can set an alarm to be alerted if the patient's glucose levels are above a defined level, such as being above 200 mg/dL for a period of time such as an hour. If data points are not coming in sequentially to the remote monitor device, it will not be able to track and issue an alarm. Moreover, if only thirty minutes of data are backfilled when the device comes back online, then it will not meet the alarm criteria since the exemplary alarm depends on an hour of data. To address this problem, the remote monitor devices can be backfilled in defined time ranges as described previously, such as six hours. The data can be sent to the remote monitoring application from oldest to newest in one embodiment. In some implementations, server(s) of the cloud computing architecture 106 such as real-time server 908 or services server 300 initiates an alert to send to a remote monitor device, such as remote monitor 316b, that indicates backfilled data is being provided. The data that is provided as backfilled data to the remote monitor device may be displayed on the remote monitor device's display differently than data provided in its normal cycle. This will help the remote monitor device know whether or not an action should be taken based on the backfilled data. Similar to the above, remote monitoring settings are configurable through the server (e.g., real-time sever 908 or services server 300). In an illustrative example, a remote monitor may not want to know that an adult or responsible person "went low" six hours earlier as that person likely took action on their own to remedy the situation. Therefore, the remote monitor device can configure the data sent in a backfill such that stale data is not displayed, the time period of the backfill is defined, backfilling from newest to oldest or from oldest to newest is defined, certain data points are not backfilled, and the like.

Generally, data is backfilled from oldest to the newest (most recent). This can cause some confusion for alarming as the oldest data begins to backfill, alarm conditions may be present. For example, glucose levels could drop to an alarm level or stay at a level that triggers an alarm after a set amount of time. However, this condition may have occurred, for example, four hours previously, when the display now receiving the backfill data was not receiving real-time data. Rather than trigger an alarm on the display 104 or the remote monitor device 316 for a remote monitor now, the server may be configured to continue to backfill data to determine if the alarm condition clears itself. Also, the server of the cloud computing architecture 106 (e.g., real-time sever 908 or services server 300) may be set such that stale backfilled alarms are not triggered unless there are rules on the server associated with particular displays that instruct it to do so. For example, the person being monitored could be a child, in which case a remote monitor (e.g., a parent) may want to know that the child experienced an alarm condition, even if it was in the past and has now corrected itself. Therefore, the parent's monitoring device (e.g., display 316) could be triggered to alarm even though the condition occurred some hours previous. The remote monitor display 316a can also be configured to indicate that the alarm is based on backfill data rather than current data.

Figure 13:
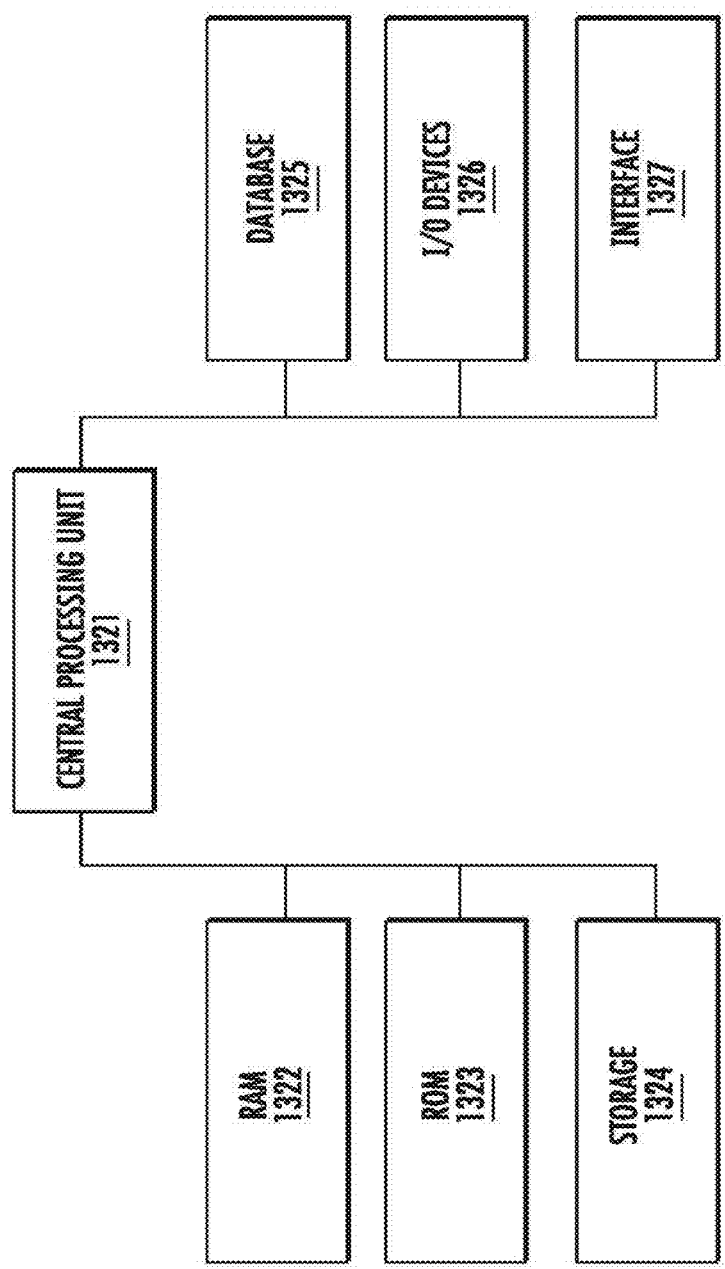
FIG. 13 illustrates an exemplary computer for use with the disclosed embodiments.

FIG. 13 illustrates an exemplary computer. Continuous glucose sensor units 100, the displays 104, computing devices of the cloud computing architecture 106 including associated servers, as well as other system components, can include all or some of the components shown in FIG. 13.

The computers may include one or more hardware components such as, for example, a central processing unit (CPU) 1321, a random access memory (RAM) module 1322, a read-only memory (ROM) module 1323, a storage 1324, a database 1325, one or more input/output (I/O) devices 1326, and an interface 1327. Alternatively or additionally, the computer may include one or more software components such as, for example, a computer-readable medium including computer executable instructions for performing a method associated with the exemplary embodiments. It is contemplated that one or more of the hardware components listed above may be implemented using software. For example, storage 1324 may include a software partition associated with one or more other hardware components. It is understood that the components listed above are exemplary only and not intended to be limiting.

CPU 1321 may include one or more processors, each configured to execute instructions and process data to perform one or more functions associated with a computer for monitoring glucose levels. CPU 1321 may be communicatively coupled to RAM 1322, ROM 1323, storage 1324, database 1325, I/O devices 1326, and interface 1327. CPU 1321 may be configured to execute sequences of computer program instructions to perform various processes. The computer program instructions may be loaded into RAM 1322 for execution by CPU 1321.

RAM 1322 and ROM 1323 may each include one or more devices for storing information associated with operation of CPU 1321. For example, ROM 1323 may include a memory device configured to access and store information associated with a controller, including information for identifying, initializing, and monitoring the operation of one or more components and subsystems. RAM 1322 may include a memory device for storing data associated with one or more operations of CPU 1321. For example, ROM 1323 may load instructions into RAM 1322 for execution by CPU 1321.

Storage 1324 may include any type of mass storage device configured to store information that CPU 1321 may need to perform processes consistent with the disclosed embodiments. For example, storage 1324 may include one or more magnetic and/or optical disk devices, such as hard drives, CD-ROMs, DVD-ROMs, or any other type of mass media device.

Database 1325 may include one or more software and/or hardware components that cooperate to store, organize, sort, filter, and/or arrange data used by CPU 1321. For example, database 1325 may data relating to monitoring glucose levels, associated metadata, and health information. It is contemplated that database 1325 may store additional and/or different information than that listed above.

I/O devices 1326 may include one or more components configured to communicate information with a user associated with a controller. For example, I/O devices may include a console with an integrated keyboard and mouse to allow a user to maintain a database of images, update associations, and access digital content. I/O devices 1326 may also include a display including a graphical user interface (GUI) for outputting information on a monitor. I/O devices 1326 may also include peripheral devices such as, for example, a printer for printing information associated with a controller, a user-accessible disk drive (e.g., a USB port, a floppy, CD-ROM, or DVD-ROM drive, etc.) to allow a user to input data stored on a portable media device, a microphone, a speaker system, or any other suitable type of interface device.

Interface 1327 may include one or more components configured to transmit and receive data via a communication network, such as the Internet, a local area network, a workstation peer-to-peer network, a direct link network, a wireless network, or any other suitable communication platform. For example, interface 1327 may include one or more modulators, demodulators, multiplexers, demultiplexers, network communication devices, wireless devices, antennas, modems, and any other type of device configured to enable data communication via a communication network.

EXAMPLES

The following examples are illustrative of several embodiments of the present technology. Other exemplary embodiments of the present technology may be presented prior to the following fisted examples, or after the following listed examples.

In some embodiments in accordance with the present technology, a method for securely transmitting data relating to glucose levels includes the following features. A continuous glucose monitor separates data into multiple categories prior to transmission. The categories can be based on whether the data identifies a patient, contains proprietary information relating to system operation (e.g., error codes, calibration formulas, raw data, calibrated data, and the like), or contains information that third-parties and other system components can access. The categories will be referred to herein as public and private data. In some embodiments, a display or a cloud computing architecture can separate data into multiple categories. The cloud computing architecture can separately store the data and restrict access to only one or more of the multiple categories of data based on the entity requesting access. Different systems can perform data synchronization at different times.

In some examples, different data streams containing different types of data can be sent separately to a server and stored separately. The data streams may be duplicative, such as where a continuous glucose monitor transmits a data stream to two connected displays, each of which forward their data (along with any other data generated by the display) to a server. This results in two separate data streams from two displays, which should be duplicative data. The cloud computing architecture stores the data streams separately, allowing it to easily grant or restrict access to the data, and also allowing the data streams to be compared to ensure correct system operation. In addition, each display can actually transmit multiple data streams where the data has been separated into one or more of the multiple categories as appropriate to allow for easy classification and permission-based access. For example, each display can send two data streams, resulting in the cloud computing architecture receiving four data streams associated with a single continuous glucose monitor. The server can then resume transmission with each particular display based on the most recently received transmissions from that display.

The continuous glucose monitor transmits the categories of data at the same or different times. For example, the continuous glucose monitor transmits some data in real-time, such as every five minutes, and other data as part of a periodic bulk transfer, such as hourly. The cloud computing architecture separately stores the real-time and bulk data. In addition, different components within the cloud computing architecture store real-time and bulk data for differing durations. This allows quick access to more recent data, such as data generated in the last thirty days, without requiring that a single server store extremely large volumes of data. Instead, the cloud computing architecture stores long-term data in separate storage.

In some exemplary embodiments, the continuous glucose monitor can encrypt at least some data prior to transmission. Encryption prevents unauthorized third-parties from accessing the data. The continuous glucose monitor encrypts some or all of the data, and only devices authorized to access a particular type of data obtain the decryption key. For example, the continuous glucose monitor transmits multiple pieces of data to a display, which only has a key to decrypt some of the data. The display forwards the data to a server that has a key used to decrypt some or all of the data. In this manner, the continuous glucose monitor encrypts private data that remains encrypted during distribution through the system until receipt by a server.

Some exemplary embodiments address a common interface for accessing the described distributed system architecture. The system or system components can be an approved medical device that may require a new approval for certain changes to system design or operation. Yet, third parties will request access to the medical data and the third-parties will use a variety of different types of requests. As third-parties create new software applications and servers, changes would need to be made to the system to grant the requested access. For example, a third-party application requests access to glucose levels in the last week to integrate the glucose levels with information regarding food consumption. Another application requests access to glucose levels to provide recommendations on insulin injections. These applications could have different interfaces and request access to different types of data (e.g., real-time v. bulk, glucose levels with or without patient identifying information, etc.). To address these issues, the cloud computing architecture implements a hub and spoke topology that provides a set of common application program interfaces. The third parties can interface with the common application program interfaces that have been granted regulatory approval. In addition, the system provides a user with a single sign-on so the user does not need to log into separate systems as a user access various system modules.

In addition, exemplary embodiments control access to a patient's medical information by remote monitors of a specific patient. A remote monitor is a person other than the patient using a continuous glucose monitor who accesses glucose levels for the patient. For example, a parent or guardian can follow their child's glucose levels and be considered a remote monitor. Maintaining confidential person-identifying information by system components can be problematic because the information may fall under HIPPA and other regulations. This could include information identifying the remote monitors themselves and location or other information identifying the remote monitors. To avoid storing identifying information about a remote monitor, the remote monitor can register with the system through an anonymous identifier generator and the system can store, for example, a unique number that associates an anonymous identification of the remote monitor with a display. The cloud computing architecture therefore does not need to receive or store any specifically identifying information for a remote monitor.

Some embodiments address challenges associated with missed transmissions of data from the continuous glucose monitor. For example, a smartphone could be turned off or out of wireless range and therefore will miss data transmissions. The display will therefore show that some data was missing, and a user may even not receive an alarm when their glucose levels dropped below or rose above a defined level due to the display being out of communication with the continuous glucose monitor. This same issue of missing data applies equally to other components throughout the system, including additional displays, third-party applications, and components in the cloud computing architecture. To address this challenge, embodiments identify when a particular device is missing data. Then, the missing data can be selectively provided to the device as part of a process referred to as backfilling. For example, a display searches for missing data within the last six hours. Upon identifying missing data, the display requests and receives the missing data from the continuous glucose monitor, another display, or another system component (i.e., "backfills" the missing data). The display or other system component searches additional time intervals also, up to a defined maximum such as one day or thirty days, depending on the component, and backfills the other missing data. Then, the display illustrates to a user which data was received as scheduled or as it was transmitted (i.e., "in time") versus data received after a delay and through the backfill process. This allows a user to readily identifying why the display did not generate an alarm at a given time, such as when the device was out of range so it did not receive any glucose levels to evaluate against the alarm limits.

Another challenge arises with distinguishing between data that was received as scheduled upon transmission or through a backfill process. When a user misses an alarm because a device was out of range, but looks at their smartphone and sees that glucose data is available in the time range of when an alarm should have issued, the user can become confused or assume there was an error with the alarm. However, the smartphone did not have the data at the time of the alarm but instead backfilled the data subsequently. To address this issue, in some embodiments, the displays and cloud computing architecture store an indication as to whether data was received as scheduled upon transmission or later as part of a backfill process. The cloud computing architecture stores the data separately along with the indication to distinguish the data for subsequent technical support and other issues. In addition, multiple displays send separate data streams to the cloud computing architecture, which the cloud computing architecture stores separately along with an indication of which display sent the data. This allows the cloud computing architecture to identify which display forwarded the data and helps identify the source of any problems.

In some aspects, a method for securely transmitting data relating to glucose levels is described. The method can comprise preparing data including glucose levels using a continuous glucose monitor; wirelessly transmitting the data relating to glucose levels to at least one display device from a transmitter associated with the continuous glucose monitor; automatically forwarding the data relating to glucose levels from the display device to a cloud computing architecture; and storing the data relating to glucose levels in separate groups at the cloud infrastructure. The data relating to glucose levels can comprise measured glucose values and diagnostic data.

Optionally or alternatively, the above-described method can further comprise including, by the display device, additional data with the data relating to glucose levels, wherein automatically forwarding the data comprises automatically forwarding the additional data and the data relating to glucose levels.

Optionally or alternatively, the data relating to glucose levels can comprise a first set of data and a second set of data, and storing the data relating to glucose levels in separate groups can comprise storing the first set of data on a first server and the second set of data on a second server. Optionally or alternatively, the first set of data can comprise real-time data, the real-time data comprising one or more of glucose values, a current status of a continuous glucose sensor, and timestamps associated with measurements used to obtain the glucose values; and the second set of data comprises at least one of information for calibrating the continuous glucose monitor and information used for technical support of the continuous glucose monitor.

Optionally or alternatively, the above-described method can further comprise encrypting the first set of data by the transmitter; encrypting the second set of data by the transmitter; decrypting and displaying the first set of data by the at least one display device; preventing the at least one display device from decrypting the second set of data; and decrypting the second set of data by the cloud infrastructure.

Optionally or alternatively, the above-described method can further comprise storing a first key to decrypt the first set of data by the at least one display device; storing a second key to decrypt the second set of data by the cloud infrastructure; and preventing access to the second key by the at least one display device.

Optionally or alternatively, the above-described method can further comprise forwarding a subset of the data relating to glucose levels from the cloud infrastructure to a second display device, the subset of data comprising at least one of current and past glucose levels.

Optionally or alternatively, the above-described method can further comprise selectively determining, by the cloud infrastructure, whether to grant access to the first set of data and the second set of data by one or more requesting systems. The requesting systems can comprise a technical support system, at least one third-party application, and a data warehouse, wherein the cloud infrastructure: grants the technical support system access to the first set of data and the second set of data; grants the at least one third-party application access to the first set of data; and grants the data warehouse access to the first set of data and the second set of data.

Optionally or alternatively, the display device can comprise at least one of a smartphone or a display.

In some aspects, a system for monitoring data relating to glucose levels is disclosed. The system can comprise a continuous glucose sensor configured to prepare data relating to glucose levels; a wireless transmitter configured to transmit the data relating to glucose levels; a display device configured to receive the transmitted data relating to glucose levels and automatically forward the data; and a cloud computing architecture configured to receive the automatically forwarded data and store the data relating to glucose levels in separate groups. The data relating to glucose levels comprises measured glucose values and diagnostic data.

Optionally or alternatively, the above-described system can be further configured to include additional data with the data relating to glucose levels; and automatically forward the additional data and the data relating to glucose levels.

Optionally or alternatively, in the above-described system the data relating to glucose levels can comprise a first set of data and a second set of data, and storing the data relating to glucose levels in separate groups can comprise separately storing the first set of data on a first server and storing the second set of data on a second server.

Optionally or alternatively, in the above-described system the first set of data can comprise real-time data, the real-time data comprising one or more of glucose values, a current status of a continuous glucose sensor, and timestamps associated with measurements used to obtain the glucose values; and the second set of data can comprise at least one of information for calibrating the continuous glucose monitor and information used for technical support of the continuous glucose monitor.

Optionally or alternatively, in the above-described system the transmitter can be further configured to encrypt the first set of data and the second set of data; the at least one display device can be further configured to decrypt and display the first set of data; the at least one display device cannot decrypt the second set of data; and the cloud infrastructure can be further configured to decrypt the second set of data.

Optionally or alternatively, in the above-described system the at least one display device can be further configured to store a first key to decrypt the first set of data; the cloud infrastructure can be further configured to store a second key to decrypt the second set of data; and the at least one display device cannot access the second key.

Optionally or alternatively, in the above-described system the cloud infrastructure can be further configured to forward a subset of the data relating to glucose levels to a second display device, the subset of data comprising at least one of current and past glucose levels.

Optionally or alternatively, in the above-described system the cloud infrastructure can be further configured to selectively determine whether to grant access to the first set of data and the second set of data by one or more requesting systems. The requesting systems can comprise a technical support system, at least one third-party application, and a data warehouse, wherein the cloud infrastructure can be further configured to: grant the technical support system access to the first set of data and the second set of data; grant the at least one third-party application access to the first set of data; and grant the data warehouse access to the first set of data and the second set of data.

Optionally or alternatively, in the above-described system the display device can comprise at least one of a smartphone or a display.

In some aspects, a computer-readable media comprising instructions which, when executed by one or more processors, perform a method for securely transmitting data relating to glucose levels is described. The instructions can comprise preparing data relating to glucose levels using a continuous glucose monitor; wirelessly transmitting the data relating to glucose levels to at least one display device from a transmitter associated with the continuous glucose monitor; automatically forwarding the data relating to glucose levels from the display device to a cloud computing architecture; and storing the data relating to glucose levels in separate groups at the cloud infrastructure. The data relating to glucose levels can comprise measured glucose values and diagnostic data.

Optionally or alternatively, the instructions may comprise including, by the display device, additional data with the data relating to glucose levels, wherein automatically forwarding the data comprises automatically forwarding the additional data and the data relating to glucose levels.

Optionally or alternatively, the instructions may comprise the data relating to glucose levels comprises a first set of data and a second set of data, and storing the data relating to glucose levels in separate groups comprises separately storing the first set of data and the second set of data by the cloud infrastructure.

Optionally or alternatively, the instructions may comprise the first set of data comprises real-time data, the real-time data can comprise one or more of glucose values, a current status of a continuous glucose sensor, and timestamps associated with measurements used to obtain the glucose values; and the second set of data can comprise at least one of information for calibrating the continuous glucose monitor and information used for technical support of the continuous glucose monitor.

Optionally or alternatively, the instructions may comprise encrypting the first set of data by the transmitter; encrypting the second set of data by the transmitter; decrypting and displaying the first set of data by the at least one display device; preventing the at least one display device from decrypting the second set of data; and decrypting the second set of data by the cloud infrastructure.

Optionally or alternatively, the instructions may comprise storing a first key to decrypt the first set of data by the at least one display device; storing a second key to decrypt the second set of data by the cloud infrastructure; and preventing access to the second key by the at least one display device.

Optionally or alternatively, the instructions may comprise forwarding a subset of the data relating to glucose levels from the cloud infrastructure to a second display device, the subset of data comprising at least one of current and past glucose levels.

Optionally or alternatively, the instructions may comprise selectively determining, by the cloud infrastructure, whether to grant access to the first set of data and the second set of data by one or more requesting systems.

Optionally or alternatively, the instructions may comprise the requesting systems comprising a technical support system, at least one third-party application, and a data warehouse, wherein the cloud infrastructure: grants the technical support system access to the first set of data and the second set of data; grants the at least one third-party application access to the first set of data; and grants the data warehouse access to the first set of data and the second set of data.

Also disclosed herein in are various embodiments of systems, methods and computer-readable media associated with securely transmitting data relating to glucose levels including, for example, a method for encrypting and transmitting data relating to glucose levels from a continuous glucose monitor, a system for encrypting and transmitting data relating to glucose levels from a continuous glucose monitor, one or more computer-readable media comprising instructions which, when executed by one or more processors, perform a method for encrypting and transmitting data relating to glucose levels from a continuous glucose monitor, a method for controlling access to data relating to glucose levels, a system for controlling access to data relating to glucose levels, one or more computer-readable media comprising instructions which, when executed by one or more processors, perform a method for controlling access to data relating to glucose levels, a method of updating data relating to glucose levels in a distributed architecture, a system for updating data relating to glucose levels in a distributed architecture, one or more computer-readable media comprising instructions which, when executed by one or more processors, perform a method of updating data relating to glucose levels in a distributed architecture, a method for synchronizing data relating to glucose levels in a distributed architecture system, a system for synchronizing data relating to glucose levels in a distributed architecture system, one or more computer-readable media comprising instructions which, when executed by one or more processors, performs a method for synchronizing data relating to glucose levels in a distributed architecture system, and the like.

Further disclosed herein is a system for securely collecting, analyzing and reporting data related to glucose monitoring levels by a plurality of continuous glucose monitors. In some aspects, the system comprises a plurality of continuous glucose monitors (CGMs); a plurality of display devices that receive data from the plurality of CGMs, wherein the data is classified into a plurality of classifications based on data type; a cloud server architecture comprising a plurality of servers that receives the data from the plurality of display devices on an intermittent basis, wherein the data routed to a particular server of the plurality of servers is determined by the data type and wherein the intermittent basis varies depending upon data type; a plurality of remote monitor display devices that receive data from one of the plurality of servers, wherein the data sent to each of the plurality of remote monitor display devices depends upon the data type and upon the display device that transmitted the data to the one of the plurality of servers and said data is sent to the plurality of remote monitor display devices immediately upon receipt by the one of the plurality of servers; and an analysis and report engine, wherein at least a portion of the data received by the plurality of servers is transmitted to the analysis and report engine, said transmitted data analyzed and reports generated by the analysis and report engine.

In some aspects, the plurality of servers that comprise the cloud server architecture comprise at least a real-time server and a bulk data collector.

In some aspects, the data types comprise real-time data and bulk data.

In some aspects, the real-time data is routed to the real-time server from the plurality of display devices and the bulk data is routed to the bulk data collector from the plurality of display devices. In some aspects, the real-time data is routed to the real-time server from the plurality of display devices at an intermittent basis that is more frequent that the intermittent basis that the bulk data is routed to the bulk data collector from the plurality of display devices. In some aspects, the real-time data is routed to the real-time server from the plurality of display devices once every five minutes and the bulk data is routed to the bulk data collector from the plurality of display devices once every hour.

In some aspects, the system further comprises a locator service, wherein the plurality of display devices connect to the cloud server architecture through the locator service.

In some aspects, at least one of the plurality of display devices comprises a smartphone.

In some aspects, at least one of the plurality of remote monitor display devices comprises a smartphone.

In some aspects, the plurality of display devices comprises at least 150,000 devices.

In some aspects, at least one of the plurality of remote monitor display devices further comprises an application that can be executed by the at least one of the plurality of remote display devices. In some aspects, the application on the at least one of the plurality of remote monitor display devices must be open and running in order to receive the data that is ready to be sent to the at least one of the plurality of remote monitor display devices, else the data that is ready to be sent to the at least one of the plurality of remote monitor display devices is held by one of the plurality of servers.

In some aspects, at least one of the plurality of remote monitor display devices that receive data from one of the plurality of servers receives a notification that data is ready to be sent to the at least one of the plurality of remote monitor display devices. The notification may comprise a text message.

In some aspects, the application that can be executed by the at least one of the plurality of remote display devices wakes when the one of the plurality of servers attempts to send the data to the at least one of the plurality of remote display devices. In some aspects, the application requests the data to be sent from the one of the plurality of servers after the application wakes.

Also disclosed is a method for securely collecting, analyzing and reporting data related to glucose monitoring levels by a plurality of continuous glucose monitors. In some aspects, the method comprises receiving, by a plurality of display devices, data from a plurality of continuous glucose monitors (CGMs); classifying the data into a plurality of classifications based on data type; transmitting the data from the plurality of display devices to a cloud server architecture comprising a plurality of servers that receives the data from the plurality of display devices on an intermittent basis, wherein the data routed to a particular server of the plurality of servers is determined by the data type and wherein the intermittent basis varies depending upon data type; receiving, by a plurality of remote monitor display devices, data from one of the plurality of servers, wherein the data sent to each of the plurality of remote monitor display devices depends upon the data type and upon the display device that transmitted the data to the one of the plurality of servers and said data is sent to the plurality of remote monitor display devices immediately upon receipt by the one of the plurality of servers; and receiving, by an analysis and report engine, at least a portion of the data received by the plurality of servers, said received data analyzed and reports generated by the analysis and report engine. In some aspects, the plurality of servers that comprise the cloud server architecture comprise at least a real-time server and a bulk data collector.

In some aspects, classifying the data into a plurality of classifications based on data type may comprise classifying the data as real-time data and bulk data. The real-time data may be routed to the real-time server from the plurality of display devices and the bulk data may be routed to the bulk data collector from the plurality of display devices.

In some aspects, the real-time data is routed to the real-time server from the plurality of display devices at an intermittent basis that is more frequent that the intermittent basis that the bulk data is routed to the bulk data collector from the plurality of display devices. For example, the real-time data may be routed to the real-time server from the plurality of display devices once every five minutes and the bulk data may be routed to the bulk data collector from the plurality of display devices once every hour.

In some aspects, the method may further utilize a locator service, wherein the plurality of display devices connect to the cloud server architecture through the locator service.

In some aspects, at least one of the plurality of display devices comprises a smartphone.

In some aspects, at least one of the plurality of remote monitor display devices comprises a smartphone.

In some aspects, the plurality of display devices comprises at least 150,000 devices.

In some aspects, at least one of the plurality of remote monitor display devices further comprises an application that can be executed by the at least one of the plurality of remote display devices. In some aspects, the application on the at least one of the plurality of remote monitor display devices must be open and running in order to receive the data that is ready to be sent to the at least one of the plurality of remote monitor display devices, else the data that is ready to be sent to the at least one of the plurality of remote monitor display devices is held by one of the plurality of servers.

In some aspects, at least one of the plurality of remote monitor display devices that receive data from one of the plurality of servers receives a notification that data is ready to be sent to the at least one of the plurality of remote monitor display devices. For example, the notification may comprise a text message.

In some aspects, the application that can be executed by the at least one of the plurality of remote display devices wakes when the one of the plurality of servers attempts to send the data to the at least one of the plurality of remote display devices. In some aspects, the application requests the data to be sent from the one of the plurality of servers after the application wakes.

Any combination of one or more computer readable medium(s) may be utilized. The computer readable medium may be a computer readable signal medium or a computer readable storage medium. A computer readable storage medium may be, for example, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. Program code embodied on a computer readable medium may be transmitted using any appropriate medium, including but not limited to wireless, wireline, optical fiber cable, RF, etc., or any suitable combination of the foregoing.

Computer program code for may be written in any combination of one or more programming languages, including an object oriented programming language such as Java, Smalltalk, C++, or the like, and conventional procedural programming languages, such as the "C" programming language or similar programming languages. The program code may execute entirely on the computing unit.

It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

While this specification contains many specific implementation details, these should not be construed as limitations on the claims. Certain features that are described in this specification in the context of separate implementations may also be implemented in combination in a single implementation. Conversely, various features that are described in the context of a single implementation may also be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products.

It should be appreciated that the logical operations described herein with respect to the various figures may be implemented (1) as a sequence of computer implemented acts or program modules (i.e., software) running on a computing device, (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein. It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A method for securely transmitting data, comprising:
preparing data including glucose levels using a continuous glucose sensor unit;
wirelessly transmitting the data relating to the glucose levels to at least one display device from a transmitter associated with the continuous glucose sensor unit;
automatically forwarding the data relating to the glucose levels from the at least one display device to a cloud computing architecture; and
storing the data relating to the glucose levels in separate groups at the cloud computing architecture, wherein the data relating to the glucose levels comprises a first set of data and a second set of data, wherein the first set of data comprises real-time data, the real-time data comprising one or more of glucose values, a current status of the continuous glucose sensor unit, or timestamps associated with measurements used to obtain the glucose values; and the second set of data comprises at least one of information for calibrating the continuous glucose sensor unit and information used for technical support of the continuous glucose sensor unit;
encrypting the first set of data by the transmitter;
encrypting the second set of data by the transmitter;
decrypting and displaying the first set of data by the at least one display device;
preventing the at least one display device from decrypting the second set of data;
decrypting the second set of data by the cloud computing architecture;
storing a first key to decrypt the first set of data by the at least one display device;
storing a second key to decrypt the second set of data by the cloud computing architecture;
preventing the second key from being accessed by the at least one display device; and
selectively determining, by the cloud computing architecture, whether to grant access to the first set of data and the second set of data by one or more requesting systems, wherein the requesting systems comprise a technical support system, at least one third-party application, and a data warehouse, wherein the cloud computing architecture:
grants the technical support system access to the first set of data and the second set of data;
grants the at least one third-party application access to the first set of data; and
grants the data warehouse access to the first set of data and the second set of data.

2. The method of claim 1, wherein the data relating to the glucose levels comprises measured glucose values and system diagnostic data.

3. The method of claim 1, further comprising:
providing, by the at least one display device, additional data with the data relating to the glucose levels,
wherein the automatically forwarding the data comprises automatically forwarding the additional data and the data relating to the glucose levels.

4. The method of claim 1,
further comprising storing the data relating to the glucose levels in separate groups comprises storing the first set of data on a first server and the second set of data on a second server.

5. The method of claim 1, further comprising:
forwarding a subset of the data relating to the glucose levels from the cloud computing architecture to a second display device, the subset of data comprising at least one of current and past glucose levels.

6. The method of claim 1, wherein the display device comprises at least one of a smartphone, tablet, desktop computer, laptop computer, wearable display device.

7. The method of claim 1, wherein the cloud computing architecture includes a plurality of servers configured to receive the data from the at least one display device, wherein the data routed to a particular server of the plurality of servers is determined by a data type including real-time data and bulk data, wherein bulk data is different than real time data and is data that is transmitted less frequently than real-time data, and is selected from the group consisting of: data about system software version information, system diagnostic information, other proprietary data, and data about stored readings recorded over a time period.

8. The method of claim 1, further comprising receiving data at a plurality of remote monitor display devices from the real-time server, wherein the data sent to a respective remote monitor display device of the plurality of remote monitor display devices is associated with a corresponding continuous glucose sensor device to which the remote monitor display device is assigned to monitor.

9. A system for monitoring data relating to analyte levels, comprising:
a continuous glucose sensor unit configured to prepare data relating to glucose levels, the continuous glucose sensor unit including a wireless transmitter configured to transmit the data relating to the glucose levels;
at least one display device configured to receive the transmitted data relating to the glucose levels and automatically forward the data; and
a cloud computing architecture configured to receive the automatically forwarded data and store the data relating to the glucose levels in separate groups, wherein the data relating to the glucose levels comprises a first set of data and a second set of data, and further wherein the first set of data comprises real-time data, the real-time data comprising one or more of glucose values, a current status of the continuous glucose sensor unit, or timestamps associated with measurements used to obtain the glucose values; and the second set of data comprises at least one of information for calibrating the continuous glucose sensor unit and information used for technical support of the continuous glucose sensor unit,
wherein the wireless transmitter is further configured to encrypt the first set of data and the second set of data, the at least one display device is further configured to decrypt and display the first set of data; the at least one display device cannot decrypt the second set of data; the cloud computing architecture is further configured to decrypt the second set of data; the at least one display device is further configured to store a first key to decrypt the first set of data; the cloud computing architecture is further configured to store a second key to decrypt the second set of data; and the at least one display device cannot access the second key; and
wherein the cloud computing architecture is further configured to selectively determine whether to grant access to the first set of data and the second set of data by one or more requesting systems, wherein the requesting systems comprise a technical support system, at least one third-party application, and a data warehouse, wherein the cloud computing architecture is further configured to:
grant the technical support system access to the first set of data and the second set of data;
grant the at least one third-party application access to the first set of data; and
grant the data warehouse access to the first set of data and the second set of data.

10. The system of claim 9, wherein the data relating to the glucose levels comprises measured glucose values and system diagnostic data.

11. The system of claim 9, wherein the at least one display device is further configured to:
provide additional data with the data relating to the glucose levels; and
automatically forward the additional data and the data relating to the glucose levels.

12. The system of claim 9,
wherein the cloud computing architecture is configured to separately store the first set of data on a first server and storing the second set of data on a second server.

13. The system of claim 9, wherein the cloud computing architecture is further configured to forward a subset of the data relating to the glucose levels to a second display device, the subset of data comprising at least one of current and past glucose levels.

14. The system of claim 9, wherein the at least one display device comprises at least one of a smartphone, tablet, desktop computer, laptop computer, wearable display device.

15. The system of claim 9, wherein the cloud computing architecture includes a plurality of servers configured to receive the data from the at least one display device, wherein the data routed to a particular server of the plurality of servers is determined by a data type including real-time data and bulk data, wherein bulk data is different than real time data and is data that is transmitted less frequently than real-time data, and is selected from the group consisting of: data about system software version information, system diagnostic information, other proprietary data, and data about stored readings recorded over a time period.

16. The system of claim 15, wherein the plurality of servers are configured to receive the data from the at least one display device on an intermittent basis that varies depending upon the data type.

17. The system of claim 15, wherein the plurality of servers of the cloud server architecture comprise at least a real-time server and a bulk data collector, the real-time server configured to receive the real-time data, and the bulk data collector configured to receive the bulk data.

18. The system of claim 17, further comprising:
a plurality of remote monitor display devices that receive data from the real-time server, wherein the data sent to a respective remote monitor display device of the plurality of remote monitor display devices is associated with a corresponding continuous glucose sensor device to which the remote monitor display device is assigned to monitor.

\* \* \* \* \*

UNITED STATES PATENT AND TRADEMARK OFFICE
CERTIFICATE OF CORRECTION

PATENT NO. : 10,085,640 B2
APPLICATION NO. : 15/152363
DATED : October 2, 2018
INVENTOR(S) : Michael Robert Mensinger It is certified that error appears in the above-identified patent and that said Letters Patent is hereby corrected as shown below:

In the Specification

In Column 8 at Line 18, Change "the a" to --the--.

In Column 24 at Line 62, Change "show in in" to --shown in--.

Signed and Sealed this
Twenty-ninth Day of January, 2019

Andrei Iancu
*Director of the United States Patent and Trademark Office*